United States Patent
Kolber et al.

[11] Patent Number: 6,121,053
[45] Date of Patent: Sep. 19, 2000

[54] MULTIPLE PROTOCOL FLUOROMETER AND METHOD

[75] Inventors: Zbigniew S. Kolber, Shoreham; Paul G. Falkowski, Stony Brook, both of N.Y.

[73] Assignee: Brookhaven Science Associates, Upton, N.Y.

[21] Appl. No.: 08/988,269

[22] Filed: Dec. 10, 1997

[51] Int. Cl.[7] .................................................. G01N 21/64
[52] U.S. Cl. .................. 436/172; 422/82.08; 250/458.1; 250/459.1; 250/461.1
[58] Field of Search .................................. 436/172, 905; 422/82.08; 250/458.1, 459.1, 461.1, 461.2

[56] References Cited

U.S. PATENT DOCUMENTS

| | | | |
|---|---|---|---|
| 3,666,945 | 5/1972 | Frungel et al. | 356/318 |
| 4,084,905 | 4/1978 | Schreiber et al. . | |
| 4,178,512 | 12/1979 | Frungel et al. | 250/461.1 |
| 4,293,225 | 10/1981 | Wheaton | 250/461.1 |
| 4,650,336 | 3/1987 | Moll | 356/417 |
| 4,698,308 | 10/1987 | Ikeda | 250/461.2 |
| 4,730,922 | 3/1988 | Bach et al. | 356/317 |
| 4,786,813 | 11/1988 | Svanberg et al. | 250/461.2 |
| 4,802,768 | 2/1989 | Gifford et al. | 356/318 |
| 4,804,849 | 2/1989 | Booth et al. | 250/459.1 |
| 4,804,850 | 2/1989 | Norrish et al. | 356/417 |
| 4,840,485 | 6/1989 | Gratton | 356/317 |
| 4,942,303 | 7/1990 | Kolber | 250/458.1 |
| 5,075,714 | 12/1991 | Hagiuda et al. . | |
| 5,107,292 | 4/1992 | Tanaka et al. . | |
| 5,130,738 | 7/1992 | Hirata . | |
| 5,159,381 | 10/1992 | Harrison . | |
| 5,180,953 | 1/1993 | Hirata et al. . | |
| 5,184,171 | 2/1993 | Uenishi . | |
| 5,187,410 | 2/1993 | Shimizu et al. . | |
| 5,323,008 | 6/1994 | Studholme et al. | 250/459.1 |
| 5,426,306 | 6/1995 | Kolber | 250/458.1 |
| 5,818,582 | 10/1998 | Fernandez et al. | 356/318 |

*Primary Examiner*—Jeffrey Snay
*Attorney, Agent, or Firm*—Margaret C. Bogosian

[57] ABSTRACT

A multiple protocol fluorometer measures photosynthetic parameters of phytoplankton and higher plants using actively stimulated fluorescence protocols. The measured parameters include spectrally-resolved functional and optical absorption cross sections of PSII, extent of energy transfer between reaction centers of PSII, $F_0$ (minimal), $F_m$ (maximal) and $F_v$ (variable) components of PSII fluorescence, photochemical and non-photochemical quenching, size of the plastoquinone (PQ) pool, and the kinetics of electron transport between $Q_a$ and PQ pool and between PQ pool and PSI. The multiple protocol fluorometer, in one embodiment, is equipped with an excitation source having a controlled spectral output range between 420 nm and 555 nm and capable of generating flashlets having a duration of 0.125–32 $\mu s$, an interval between 0.5 $\mu s$ and 2 seconds, and peak optical power of up to 2 W/cm$^2$. The excitation source is also capable of generating, simultaneous with the flashlets, a controlled continuous, background illumination.

34 Claims, 21 Drawing Sheets

MULTIPLE PROTOCOL FLUOROMETER AND METHOD

This invention was made with Government support under contract number DE-AC02-76CH00016, between the U.S. Department of Energy and Associated Universities, Inc. The Government has certain rights in the invention.

BACKGROUND OF THE INVENTION

1. Field of the Invention

The invention relates generally to fluorometers, instruments for measuring wavelength and intensity of fluorescence. More particularly, the invention relates to a multiple protocol fluorometer (MPF) for measuring photosynthetic parameters of phytoplankton and higher plants using an actively stimulated fluorescence signal.

2. Description of the Related Art

Measurement of photosynthetic activity that occurs in photosynthetic organisms such as phytoplankton or higher plants is important in understanding the basic physiology of phytoplankton and higher plants, as well as to ecological studies of environmental stress. In ocean studies, for instance, characterization of photosynthesis of phytoplankton is useful in (i) understanding the ocean carbon cycle, (ii) predicting how climate-induced changes in ocean circulation, as well as, anthropogenic perturbation affect ocean productivity, and vice versa, and (iii) understanding how oceans can mediate climate change.

Furthermore, in terrestrial applications, measurements of photosynthetic parameters can be used to (i) assess effects of the environmental factors (nutrients limitation, drought, temperature) on plants' physiological performance, (ii) select and evaluate crop strains with respect to resistance to natural and anthropogenic stresses, (iii) assess physiological response of plants to contamination insults (chemicals, heavy metals, low level radioactive wastes), and (iv) evaluate the efficacy of remediation efforts with respect to restoring the ecological status of contamination threatened ecosystems.

Assessment of photosynthesis by photosynthetic organisms requires either a direct measurement or an indirect approach based on measurement of photosynthetic parameters. Direct measurements of photosynthesis of phytoplankton or higher plants include those of $CO_2$ exchange, $O_2$ evolution, or radioactive labelled carbon incorporation (i.e., $^{14}C$ method). However, these measurements are laborious, time consuming, and not applicable in certain conditions. In studying phytoplankton, for example, the $^{14}C$ measurement method requires an incubation and can be done only for discrete, bottled samples. Further, accuracy in photosynthesis measurements of phytoplankton in laboratory settings are limited as a result of removal of the phytoplankton from its normal ambient nutrient flux, and laboratory simulation of ambient light and temperature conditions. In terrestrial applications, where the $CO_2$ exchange method is the only applicable measurement, extensive sample manipulations are required, resulting in a measurement process that itself modifies the investigated photosynthetic parameters.

Indirect measurements of photosynthesis, based on a functional relationship between photosynthetic activity and fluorescence, have proven to be more successful. Such indirect measurement methods include both passive fluorescence and active fluorescence techniques.

Passive fluorescence techniques are flawed by an assumption that the ratio of the photosynthetic to fluorescence yield is constant. In nature, this ratio can vary by as much as 10:1, making the passive fluorescence based estimates of photosynthesis unreliable. More detailed measurement and study of photosynthetic processes, such as light absorption, primary photochemistry, and electron transport between so-called Photosystem II (PSII), and Photosystem I (PSI), are not possible with passive fluorescence techniques.

Active fluorescence techniques, on the other hand, are based on flash stimulated fluorescence. An example employing an active fluorescence technique, is disclosed in Moll, U.S. Pat. No. 4,650,336, which describes a method and device for measuring photosynthesis, specifically variable fluorescence of plants. Variable fluorescence is measured as the difference between a low level, steady state fluorescence and a higher level of a fluorescent transient. The fluorometer device of Moll has one lamp to provide constant-level light to bring about continuous, steady state fluorescence of a plant, and a flash lamp to provide a flash of light (excitation energy) to bring about a transient fluorescence of the plant. The device and method of Moll utilize the second flash lamp to produce either a single flash, or series of flashes at a slow repetition rate, approximately one hundred (100) Hz. At 100 Hz, however, the flash rate is too slow to effectively measure the photosynthetic processes occurring in photosynthetic organisms.

Another active fluorescence technique is described in Kolber et al., U.S. Pat. No. 4,942,303 (Kolber I), the contents of which are incorporated, in its entirety, by reference herein. The technique described in Kolber I enables a more detailed measurement of photosynthesis. Specifically, the technique involves use of "pump and probe" flashes for measuring the change in fluorescence of phytoplankton or higher plants. A relatively low intensity probe flash is followed quickly by a pump flash that is usually made intense enough to saturate PSII.

Kolber I also discloses a computer controlled fluorometer device and method that measures photosynthesis by monitoring and recording changes in fluorescence produced by a computer controlled series of cycles of probe and pump flashes. From these measurements, various photosynthetic parameters can be determined and incorporated into a mechanistic model of photochemistry based on the kinetics of electron flow between PSII and PSI.

The pump and probe technique, although very successful in measuring the photosynthesis occurring in phytoplankton or higher plants, has the following operational limitations:

1. In order to measure the absorption cross-section and the rate of electron flow from PSII to PSI the pump and probe fluorometer employs a sequence of probe, pump, and probe flashes, repeated up to 30 times, with the intensity of the pump flash changed from zero to a supersaturating level, or with the delay between the pump, and the second probe flash changing from 80 μs to 300 ms. These two protocols require 5 minutes to 10 minutes of fluorometer operation in order to make appropriate measurements. Particularly, when the pump and probe technique is used in a profiling mode for studying phytoplankton in the ocean, where these protocols often have to be executed at every meter of a water column, the time required for making the measurements is prohibitively long.

2. The intensity of the probe flash has to be kept below 1% of the PSII saturation level. This low intensity flash results in a low signal to noise ratio, particularly at low chlorophyll concentrations.

3. The pump and probe fluorometer requires two separate excitation channels (i.e., two flashers) which complicates construction, and increases the cost of the fluorometer.

4. Execution of a full experimental protocol, particularly in studying phytoplankton in the ocean, utilizes a large amount of electrical power. This requirement limits long-term, remote mooring applications where electrical batteries are used to power the fluorometer.

Kolber et al., U.S. Pat. No. 5,426,306 (Kolber II), the contents of which are incorporated, in its entirety, by reference herein, discloses a fast repetition rate (FRR) fluorometer that is operable to produce a series of fast repetition rate flashes in the range of 10,000 Hz to 250,000 Hz, and at controlled energies sufficient to gradually and incrementally effect photosynthetic processes occurring in PSII and PSI in phytoplankton or higher plants, for measurement of fluorescence with higher signal to noise ratios relative to the device of Kolber I. The FRR fluorometer of Kolber II, however, has the following disadvantages:

1. The methodology and the instrument disclosed in Kolber II has a limited resolution of the saturation and fluorescence decay, because the flash rate of the xenon flashlamp in the FRR fluorometer is limited to 250 kHz. When there is pre-triggering prior to each flash, the maximum flash rate falls below 10 kHz. Therefore, the FRR fluorometer is incapable of resolving the initial portion of the fluorescence transient that is critical for assessment of the faster photosynthetic processes such as the extent of energy transfer between PSII reaction centers. Due to the same limitation, only the early stage of fluorescence decay can be measured, thus limiting the resolution of the assessed kinetics of electron transport in PSII to a single time constant.

2. The power dissipation by the xenon flashlamp in the FRR fluorometer is excessive and limits the measurement protocols that can be used with the FRR fluorometer. For example, when generating flashes at intervals of 60–100 µs, the xenon plasma must be reheated using about 2 µs-long high current pulse (average 200 A at 400 V), dissipating about 0.16 J of energy per flash. The power rating of xenon flashlamp used in FRR fluorometer is about 15 W, thus limiting the number of flashes to less than 100 flashes. Furthermore, the excessive power dissipation limits long-term, remote mooring applications where electrical batteries are used to power the fluorometer, such as, for example, in a submersible instrument with a dual, self-cleaning chamber, discussed further herein.

3. Assessment of the correct functional absorption cross section, and the correct kinetics of electron transport within PSII and from PSII to PSI requires knowledge of the extent of energy transfer between PSII reaction centers, which cannot be measured with the FRR fluorometer.

4. The FRR fluorometer is incapable of spectrally resolving the functional absorption cross section or the extent of energy transfer between PSII reaction centers.

5. The xenon flashlamp in the FRR fluorometer cannot provide ambient illumination.

6. The xenon flashlamp in the FRR fluorometer is a pulsed light source using high voltage electronics in which large switching currents at high voltages cause a high level of RF noise.

SUMMARY OF THE INVENTION

One of the objects of the invention is to alleviate the problems and limitations identified above by providing a multiple protocol fluorometer (MPF) for accurately measuring photosynthetic parameters relating to photosynthetic processes of phytoplankton and higher plants using actively stimulated fluorescence.

Another object of the invention is to provide a multiple light emitting diode (multi-LED) excitation source that generates a uniform distribution of excitation energy within a sample volume/area.

Still another object of the invention is to provide a flasher circuit which allows measurements of the photosynthetic parameters under software-controllable levels of ambient irradiance, using the same light source to generate both the excitation flashes and the ambient illumination.

Still another object of the invention is to provide a self-cleaning chamber for the MPF for long-term unattended operation.

Still another object of the invention is to provide a submersible self-cleaning chamber for the MPF for longterm unattended operation inside bodies of water.

These and other objectives are achieved by providing a MPF equipped with an excitation source which in one embodiment has a controlled spectral output from about 420 nm to about 555 nm and is capable of generating flashlets having a duration of about 0.125–32 µs, an interval between about 0.5 µs and about 2 seconds, and peak optical power of up to 2 W/cm$^2$. (Hereinafter, a "flashlet" shall mean a single pulse of light of a specified duration, and a "flash" shall mean a sequence of flashlets with controlled time intervals between the flashlets). The excitation source is also capable of generating, simultaneous with the flashlets, a continuous, background (ambient) illumination in the 420 nm to 555 nm range at a power level controlled from zero to 50 mW/cm$^2$, and far red illumination at 720 nm at power level controlled from zero to 10 Mw/cm$^2$.

An excitation source in one embodiment is a plurality of light emitting diodes (LED's). The LED's replace the xenon flashlamps used in the FRR fluorometer. In general, the xenon flashlamp produces higher excitation energy than LED's, but at a cost of much higher power dissipation, and much less flexible excitation protocols. To match the excitation energy of the xenon flashlamps, one embodiment of the present invention provides 108 LED's, operating at 400 mA pulsed current each, are arranged into a multi-spectral LED flasher. The LED flasher is capable of generating flashlets having any duration within about 0.125–32 is, a time interval between flashlets of about 0.5 µs and 2 seconds, and variable intensity. This is because an LED is a continuous waveform light source, generating light responsive to a current flow. In the MPF according to the invention, a flasher circuit is provided to permit the LEDs to be operated in a pulsed mode generating about 10 times higher pulse intensity than is possible in the continuous waveform mode.

In another embodiment, the excitation source can be a laser diode operating at a wavelength of between about 650–670 nm. The MPF with laser diodes allow remote measurement of the photosynthetic parameters at a distance of about 1–10 meters.

At least four novel excitation protocols have been developed to exploit the characteristics of an LED-based excitation source and are implemented in the MPF to measure various photosynthetic parameters of phytoplankton and higher plants. The measured photosynthetic parameters include spectrally-resolved effective absorption cross section of PSII, extent of energy transfer between reaction centers of PSII, $F_0$ (minimal), $F_m$ (maximal) and $F_v$ (variable) components of PSII fluorescence, quantum yield of photosynthesis, photochemical and non-photochemical quenching, size of the plastoquinone (PQ) pool, and the kinetics of reduction/reoxidation at various stages of electron transport from PSII to a terminal electron acceptor.

The first protocol has six phases. In Phase I, the measured sample is excited with about 60–100 flashlets having a duration of about 0.5–1 μs each and time intervals ranging from about 0.5 μs to 2.0 μs (equivalent to frequencies of 0.5–2.0 MHz) to saturate PSII reaction centers in the sample within about 40–80 μs. In Phase II, the measured sample is excited with about 60–100 flashlets having a duration of about 0.125–0.5 μs each and time intervals exponentially increased from about 50 μs to 20 ms for a relaxation in the fluorescence yield. In Phase III, the measured sample is excited with about 2000–4000 flashlets having a duration of about 0.5–4 μs each and time intervals ranging from about 20 μs to 100 μs. The desired effect of Phase III is the reduction of the PQ pool which results in an increase of the fluorescence yield in the sample above the saturation level reached in Phase I. In Phase IV, the measured sample is excited with about 60–100 flashlets having a duration of about 0.125–0.5 μs each and time intervals exponentially increased from about 50 μs to 40 ms. In Phases V and VI, the first two phases are repeated.

The second protocol repeats Phases I and II from the first protocol about 15–30 times with about 40–80 flashlets. In this protocol, for each time that Phases I and II are repeated, the duration of Phase II ranges from about 200 μs to 10 ms.

In the third protocol, the measured sample is excited with about 2000–10000 flashlets and each flashlet length and each time interval between the flashlets is individually controlled, while the flashlet intensity remains constant. Therefore, the average excitation intensity can be controlled over several orders of magnitude, and, thereby, allowing control of the rates of PQ pool reduction.

In the fourth protocol, the measured sample is excited with a sequence of flashlets and, based on the measured fluorescence signal of the excited sample, the excitation is continuously adjusted by varying the number of flashlets, flashlet length and/or time intervals between flashlets so as to maintain the measured fluorescence signal at a predetermined level.

Additional alternative protocols that combine or modify one of more of the above described protocols are also provided by the present invention.

It will be noted that this present invention is not limited to its application to measurement of fluorescence solely in photosynthetic organisms, but may be applied to any chemical or biological analyses based on fluorescence.

Additional objects, features and advantages of the invention will become apparent from the description of preferred embodiments described below.

BRIEF DESCRIPTION OF THE DRAWINGS

In the drawings, wherein similar reference characters denote similar elements throughout the several views.

The accompanying drawings, which are incorporated in and constitute a part of the specification, illustrate presently preferred exemplary embodiments of the invention, and, together with the general description given above and the detailed description of the preferred embodiments given below, serve to explain the principles of the invention.

DETAILED DESCRIPTION OF THE PREFERRED EMBODIMENTS

1. Theory of MPF Operation

The yield of chlorophyll fluorescence in higher plants and algae is controlled by their ability to utilize light for photosynthesis. This photosynthetic performance can be assessed by measuring changes in the chlorophyll fluorescence signal f(t), in response to excitation light I(t).

The functional relationship between f(t) and I(t) is determined by biophysical processes within Photosystem II (PSII) and Photosystem I (PSI) that control the distribution of excitation energy between photosynthesis, fluorescence, and heat. These processes can be examined, and photosynthetic parameters can be quantified, by exploring the relationship between the applied excitation signal and the measured fluorescence response.

Figure 1:
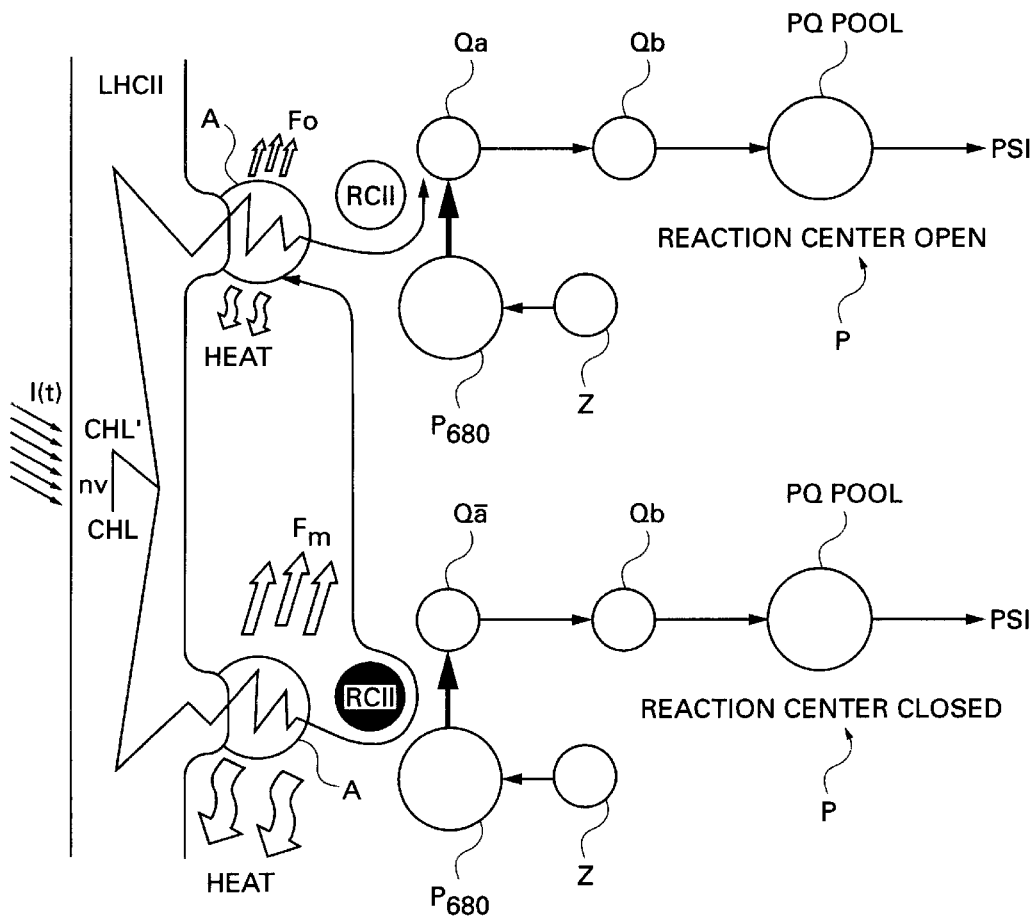
FIG. 1 is a simplified model of the photosystem II (PSII)

The fluorometry used in the invention can be explained using a simplified diagram of PSII as shown in FIG. 1. Generally, the quanta of light I(t) generated from an excitation protocol are absorbed by a light absorbing pigment LHCII, and transferred to antenna pigments A. Molecular organization of the LHCII/A permits cooperative light collection, either by sharing a common pool of LHCII (or a fraction thereof), or by exchanging excitation energy between antenna pigments A. The overall efficiency of light trapping and excitation transfer to the reaction center is described by the functional absorption cross section apsn, while the level of pigment cooperation (or pigment connectivity) is quantified in terms of probability of energy transfer between PSII reaction centers p. Excitation energy arriving at open PSII reaction centers (reaction center with the electron acceptor Qa in an oxidized state) initiates a photochemical act, resulting in reduction of Qa and oxidation of an electron donor $P_{680}$, with relatively little energy dissipated as heat and fluorescence.

As a result, the fluorescence yield in an open PSII reaction center is at minimal level $F_0$. Oxidized $P_{680}$ is reduced within about 100 ns by an electron donor Z, while reoxidation of Qa⁻ proceeds via a series of successive electron transport to Qb, PQ pool, and PSI. On an average, this latter process takes from 0.6 to 5 milliseconds, depending on the level of photosynthetic activity. During this time PSII reaction center remains closed (Qa in reduced state), and the next arriving excitation will either be dissipated in a process of fluorescence/thermal deactivation, or transferred to another PSII reaction center. Because the probability of energy transfer is significantly lower than 1 ($0<p<0.6$ in most observed cases), the fluorescence yield in a closed PSII reaction center increases above the $F_0$ level. Within a large population of PSII reaction centers, the observed fluorescence signal f(t) changes from $F_0$ to $F_{m-}$ (a maximum level) in proportion to the fraction of closed reaction centers. This fraction is controlled by the rate of excitation delivery to PSII reaction centers, defined by the product of $I(t)\sigma_{PSII}$, and by the kinetics of Qa reoxidation, defined by the rates of electron transport from Qa to PQ pool.

In the MPF, a plurality of excitation patterns are programmed and selected to stimulate the chlorophyll fluorescence signal. By selecting appropriate excitation protocols, it is possible to selectively reduce electron carriers Qa, Qb, and PQ pool. In particular, the MPF excitation protocols are designed to:

- reduce (close) all PSII reaction centers within 40 to 80 $\mu s$, with negligible amount of electrons transferred from Qa to Qb (single electron turnover saturation);
- reduce PQ pool with a sequence of electron transfers from Qa to PQ pool;
- measure the kinetics of Qa reoxidation following the reduction of Qa⁻ or PQ pool;
- assess the number of electron equivalents required to reduce the PQ pool;
- manipulate the level of photosynthetic activity within PSII and PSI by background illumination in the blue-green spectral region, and far-red spectral region; and
- measure spectrally resolved optical absorption cross section.

Interpretation of the fluorescence transients induced by MPF excitation protocols allows calculation of a range of photosynthetic parameters such as $F_0$ (minimal), $F_m$ (maximal) and $F_v$ (variable) components of PSII fluorescence, functional absorption cross section and the probability of energy transfer between PSII reaction centers, kinetics of electron transfer between different electron carriers in PSII, and the size of PQ pool. Exciting PSII at different wavelengths allows a spectral resolution of both the $\sigma_{PSII}$ and p. Ability to simultaneously manipulate the level of photosynthetic activity by controlling the background irradiance allows assessment of photochemical and non-photochemical quenching.

Following the model of PSII in FIG. 1, the stimulated florescence signal f(t), observed during a MPF excitation protocol can be expressed as a function of the excitation signal I(t), effective absorption cross section, $\sigma_{PSII}$, extent of energy transfer between PSII reaction centers p, and by the kinetics of Qa reoxidation.

Formally, the fluorescence yield f(t) observed during excitation protocol can be described as:

$$f(t) = \left[F_o + (F_m - F_o)\left(c(t)1 - \frac{p}{1 - C(t)p}\right)\right]\Psi_{Qb}(t) \quad [1]$$

where $F_0$ is the minimal fluorescence yield observed when all PSII reaction centers are open, $F_m$ is the maximum fluorescence yield observed when all PSII reaction centers are closed, C(t) is a fraction of PSII reaction center that are closed at a given stage of the excitation protocol, and $\Psi_{Qb}$(t) is the modulation of fluorescence yield due to occupation of Qb site in Qa. $\Psi_{Qb}$(t) is mostly controlled by the size of PQ pool, and by the equilibrium between the rate of electron flow into the pool, and the rate of PQ pool reoxidation. C(t) is controlled by the rate of excitation delivery to PSII reaction centers, and by the rate of $Q_a$ reoxidation in accordance with the following equation:

$$C(t) = \sigma_{PSII} \int_0^\tau I(v) \frac{1 - C(v)}{1 - C(v)p} g(t - v) dv \quad [2]$$

where g(t–v) is a function describing the kinetics of Qa reoxidation at a given stage of the excitation protocol, which generally can be expressed as a sum of up to four exponential components:

$$g(t) = \alpha_1 \exp(-t/\tau_1) + \alpha_2 \exp(-t/\tau_2) + \alpha_3 \exp(-t/\tau_3) + \alpha_4 \exp(-t/\tau_4) \quad [3]$$

Photosynthetic parameters are calculated by fitting the fluorescence profile generated during the excitation protocol into a set of Eqn. [3]. Because of the nonlinear nature of Eqn. [3], an analytical solution describing the fluorescence signal as a function of I(t) does not exist. However, using fast flashlet rates and high rates of analog-to-digital conversion (16 MHZ at 10 bits), Eqn. [3] can be expressed in a discrete, recursive form:

$$f_n = \left[F_o + (F_m - F_o)C_n \frac{1 - p}{1 - C_n p}\right]\Psi_{Qb,n} \quad [4]$$

where $f_n$ is the n-th fluorescence sample, and $\Psi_{Qb,n}$ represents changes in the fluorescence yield due to Qb site occupation during n-th sampling period. $C_n$, the fraction of PSII reaction centers closed during n-th sampling period, can be expressed as follows:

$$C_n = C_{n-1} \sum_{k=1}^{4} A_{n,k} + I_n \sigma_{PSII} \left(1 - \frac{C_{n-1} \sum_{k=1}^{4} A_{n,k}}{1 p C_{n-1} \sum_{k=1}^{4} A_{n,k}}\right) \quad [5]$$

where $I_n$ is the excitation energy delivered at n-th sampling period, and the parameter $A_{n,k}$ is determined by the kinetics of Qa or PQ pool reoxidation:

$$A_{n,k} = (A_{n-1,k} + C_{n-1}\alpha_k/\sigma_{PSII}) \exp(-\Delta t/\tau_k) \quad [6]$$

where $\alpha_k$ and $\tau_k$ describe the time constant of QA or reoxidation (Eqn. [3]), and $\Delta t$ is the sampling period. $A_{0,k}$ and $C_0$ define the initial conditions representing the fraction of PSII reaction centers closed prior to the excitation protocol. In darkness, $A_{0,k}$ and $C_0$ are equal to zero, while when measured under background irradiance, they describe a fraction of PSII reaction centers closed by the presence of ambient light. All the photosynthetic parameters are retrieved by fitting the observed $f_n$ into Eqn 4–6 using standard methods of numerical analysis.

When the rate of excitation absorption by PSII greatly exceeds the rate of Qa⁻ reoxidation (i.e. at high excitation energies, or when Qa⁻ reoxidation is blocked), Eqn. [2] can be expressed as:

$$C(t) = \sigma_{PSII} \int_0^\tau I(v) \frac{1 - C(v)}{1 - C(v)p} dv = \sigma_{PSII} \int_0^\tau I(v) \frac{F_m - f(t)}{F_m - F_o} dv \quad [7]$$

allowing approximation of $\sigma_{PSII}$ as:

$$\sigma_{PSII} = \left(\left[\int_0^\infty I(t)\frac{F_m - f(t)}{F_m - F_o}dt\right]\right)^{-1} \quad [8]$$

or in a discrete form, $$\sigma_{PSII} = \left(\left[\sum_{i=0}^N I_n F_m - \frac{f_n}{F_m - F_o}\right]\right)^{-1} \quad [9]$$

where N is the number of sampling periods from the beginning of excitation protocol to the point where fluorescence yield saturates.

The estimate of $\sigma_{PSII}$ given by Eqn. [9] serves as the initial guess for the functional absorption cross section in the fitting algorithm. The $\sigma_{PSII}$ measured by the MPF is a functional absorption cross section, i.e, it is a measure of the maximal efficiency of light utilization for photochemistry in PSII in units of $m^2$/quanta utilized for photochemistry:

$$\sigma_{PSII} = \left.\frac{\partial C}{\partial I}\right|_{C=0}, \quad [10]$$

By comparison, the maximum quantum yield of photochemistry, $\Phi_p$, is defined as:

$$\Phi_P^{max} = \left.\frac{\partial C}{\partial (Ia_{PSII})}\right|_{C=0} = \frac{\sigma_{PSII}}{a_{PSII}} = \frac{F_m - F_o}{F_m}, \quad [11]$$

where $a_{PSII}$ is the optical absorption cross section of PSII, in units of $m^2$/quanta absorbed by the photosynthetic pigment.

By measuring $\sigma_{PSII}$ and the $F_m$ and $F_0$ signals, the MPF according to the invention allows calculation of the optical absorption cross section, $a_{PSII}$. Assessment of $a_{PSII}$ based on the traditional measurement of light absorbed is difficult in aquatic environment due to the low concentration of the absorber and high scattering coefficient. Measurement of light absorbed in higher. plants is further complicated due to light absorption by the leaf tissue. The MPF approach to $a_{PSII}$ measurement based on Eqns. 10 and 11 avoids these problems.

2. Structure of MPF

Figure 2:
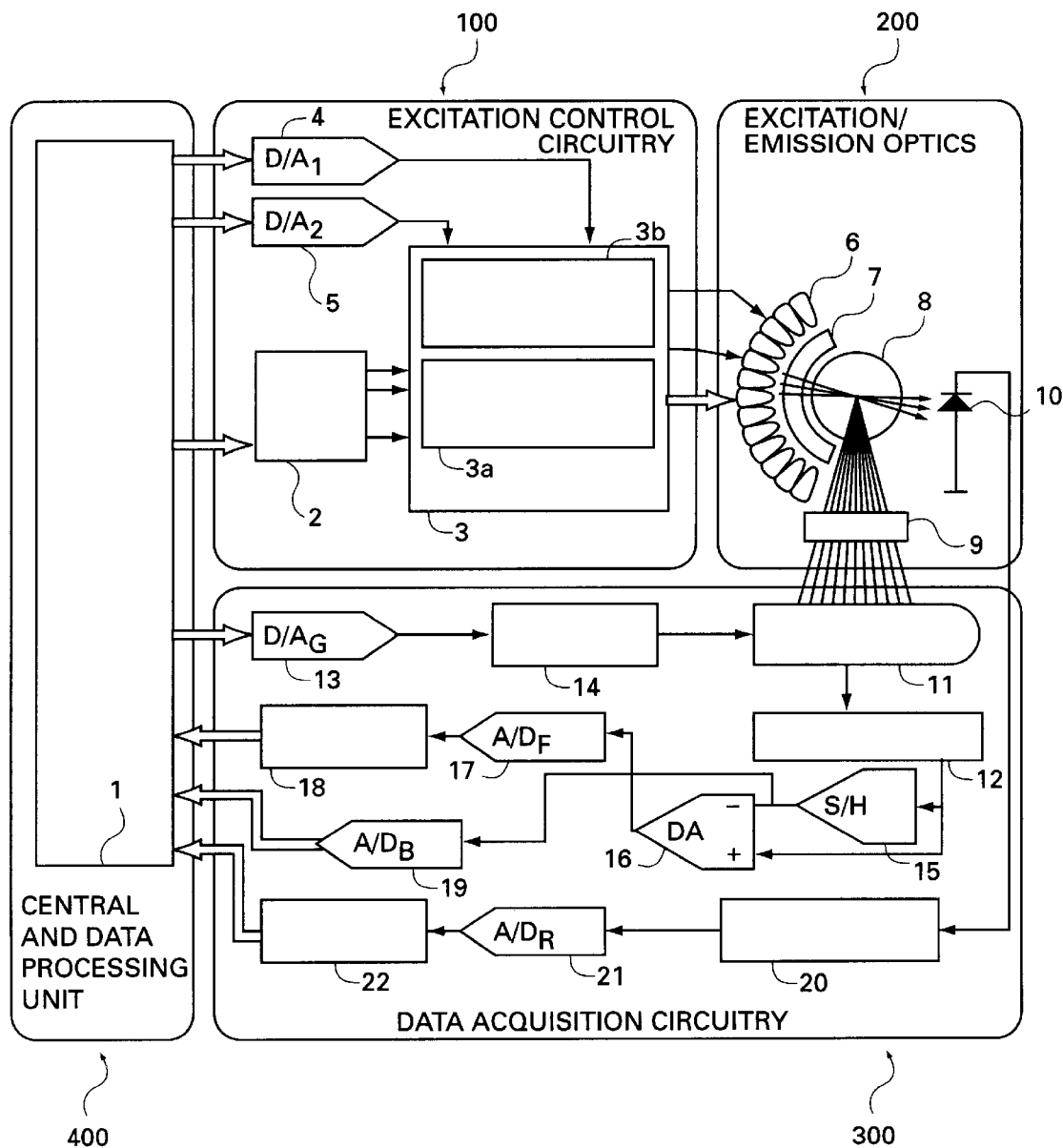
FIG. 2 is a schematic block diagram and associated optical apparatus of a multiple protocol fluorometer (MPF) according to the invention.

The four basic components of the MPF according to the invention are shown in a schematic diagram of the MPF illustrated in FIG. 2. The four basic components are: (1) excitation control circuit 100, (2) excitation/emission optics 200, (3) data acquisition circuit 300, and (4) control and data processing unit 400 which includes a controller 1 for coordinating the overall operation of the MPF.

The excitation protocols of the MPF are defined to include a sequence of up to 32000 light flashlets individually programmable to have a duration from 0.125 $\mu$s to 32 $\mu$s, a time interval from 0.5 $\mu$s to 2 seconds, and peak optical power of up to 2 W/cm$^2$.

Prior to generating an excitation sequence, an excitation protocol is selected by the controller 1 and stored in a flash timer circuit 2. The timing signals from the flash timer circuit 2 are forwarded to a flasher 3, in particular to a flash control section 3a of the flasher 3, which generates current pulses for driving an excitation source, such as a multi-spectral LED flasher 6. Other embodiments of the excitation source are possible and can include, for example, a laser diode.

The background irradiance in the blue-green spectral range (420 nm<$\lambda$<555 nm) and infrared spectral range region (700 nm<$\lambda$<740 nm) is controlled by digital-to-analog converters D/A$_1$ 4 and D/A$_2$ 5, and by a background light control section 3b of the flasher 6. The excitation light, after being filtered by an excitation filter 7, reaches a sample chamber 8 containing a measured specimen. The emitted fluorescence light is filtered by an emission filter 9, detected by a fluorescence detector 11, and amplified by a fluorescence amplifier 12 (see details in FIG. 7). The sensitivity of the fluorescence detector 11 is controlled by a digital-to-analog converter, D/A$_G$ 13, and a detector gain control circuit 14. The output from fluorescence preamplifier 12 is processed by a sample-and-hold circuit, S/H 15, and a differential amplifier, DA 16, to separate the ac (fluorescence response to excitation flashlets) and dc (fluorescence response to background illumination) components in the fluorescence signal. The ac component is digitized by a fast analog to digital converter, A/D$_F$ 17, and temporarily stored in the fluorescence RAM (random access memory) 18. The dc component is digitized by an analog-to-digital converter A/D$_B$ 19. The excitation signal is measured by a reference detector 10, amplified by a reference amplifier 20, digitized by an analog-to-digital converter A/D$_R$ 21, and stored in a reference RAM 22. After completion of the excitation sequence, the digitized fluorescence and reference signals are read into the controller 1, and processed to calculate the photosynthetic parameters of the measured sample.

Controller

Several version of the MPF controller can be implemented. In applications where minimum power consumption is required, such as in a battery powered submersible instrument intended for a long-time moored applications, TATTLETALE model 8 SBC (single board computer) from Onset Computer can be used. In portable applications, where speed of data processing is more important than low power consumption, a 486 or Pentium-based PC/104 SBC, commercially available from WinSystems can be used. In a benchtop or laboratory application, a notebook PC, Slimnote 5 with THK1004 docking station from Twinhead, or Toshiba TECRA 700 with PA2712U docking station can be used. Optionally, a PCI interface available with notebook PC may be used to interface the fluorometer circuit with the notebook PC. Persons skilled in the art would recognize that other suitable processor implementations may be used as the controller in accordance with the invention.

Flash Timer Circuit

Figure 3:
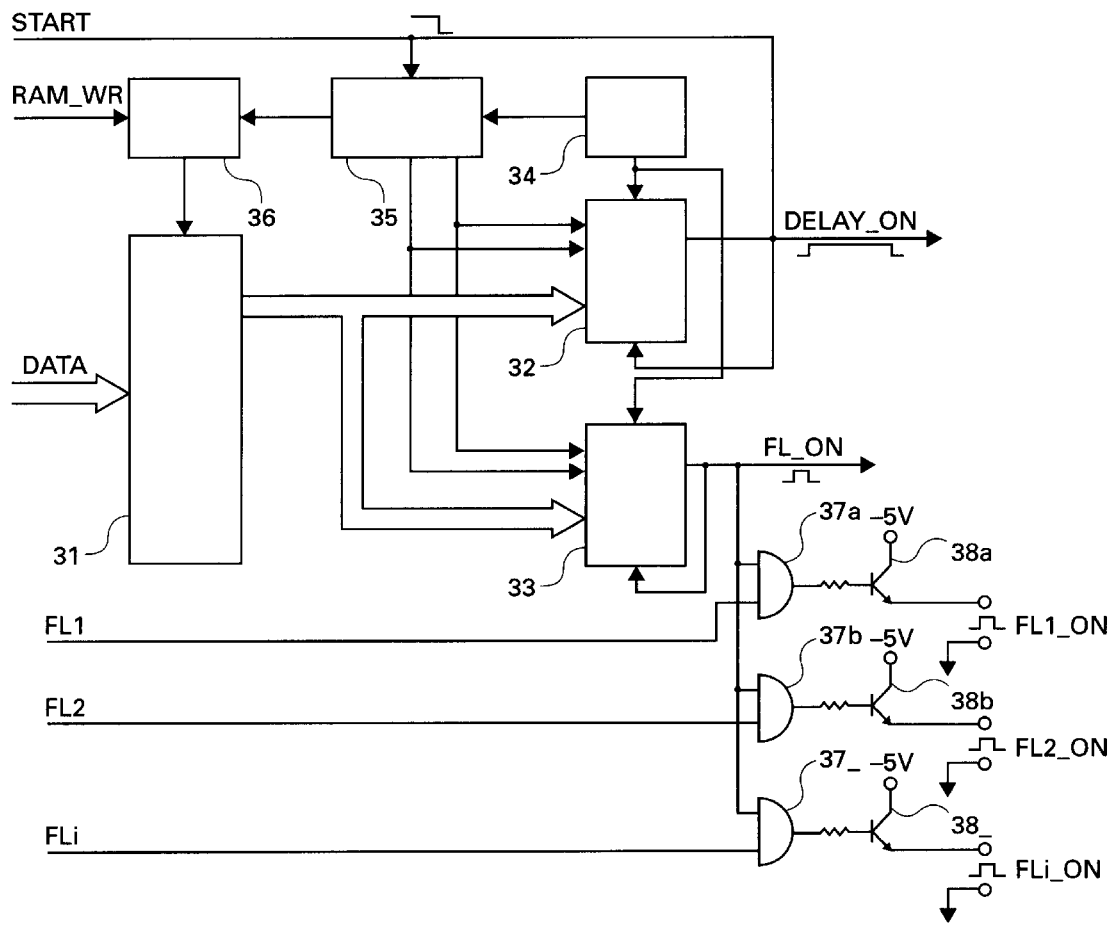
FIG. 3 is a schematic block diagram of a flash timer circuit of the MPF shown in FIG. 1.

A schematic block diagram of the flash timer circuit 2 is shown in FIG. 3. The excitation protocol (number of flashlets, flashlet length, and time interval between flashlets) is downloaded to a RAM 31 (e.g., HM628128LP-7 from Hitachi), for example, as a sequence of four bytes per flashlet. Destination addresses for download operation are determined by the address counter 36, which is updated by a write signal (RAM_WR) from the controller 1. The excitation sequence is triggered by the start signal (Start) from the controller 1 which initiates four sequential data transfer operations from the RAM 31 to counters 32 and 33, controlled by a clock 34, a four-pulse generator 35, and the address counter 36. During the first transfer, a single byte is loaded into the flash length counter 33, and a FL_ON signal is initiated. The next three transfers load the flash delay counter 32 with three bytes, and initiate a Delay_ON signal. After setting the Flash_ON and Delay_ON signals, both counters 32 and 33 count down the pulses from the clock 34. Upon receiving the number of clock pulses equal to the preset flashlet length, the FL_ON signal is terminated. The Delay_ON signal is terminated upon receiving the number of pulses equal to the designated time delay between flashlets. Termination of the Delay_ON signal initiates the next 4-byte read sequence, and generation of a subsequent FL_ON and Delay_ON signals, until all of the flashlets in the excitation sequence are generated.

The flash timer circuit 2 according to FIG. 3 can be implemented using, for example, a standard logic circuit for a portable/benchtop MPF design, or using, for example, a Field Programmable Gate Array (FPGA) (e.g., AT6005 from Atmel) in a submersible MPF design.

To selectively activate the flasher section with a different spectral output, the Flash_ON signal is gated with FL1, FL2, . . . , Fli signals using AND gates 37a, 37b, . . . , 37_ (where i=the number of flasher sections). Flash_ON signals are forwarded to the flash driver via transistors 38a, 38b, . . . , 38_ (e.g., 2N4401 from Texas Instrument). Optionally, open collector gates can be used instead of transistors 38a, 38b, . . . , 38_, or the gated FL_ON signals (FL1_ON, FL2_ON, . . . , FLi_ON) can be interfaced directly to the flasher circuit 3, at the cost of lower noise immunity.

Flasher Circuit

Figure 4:
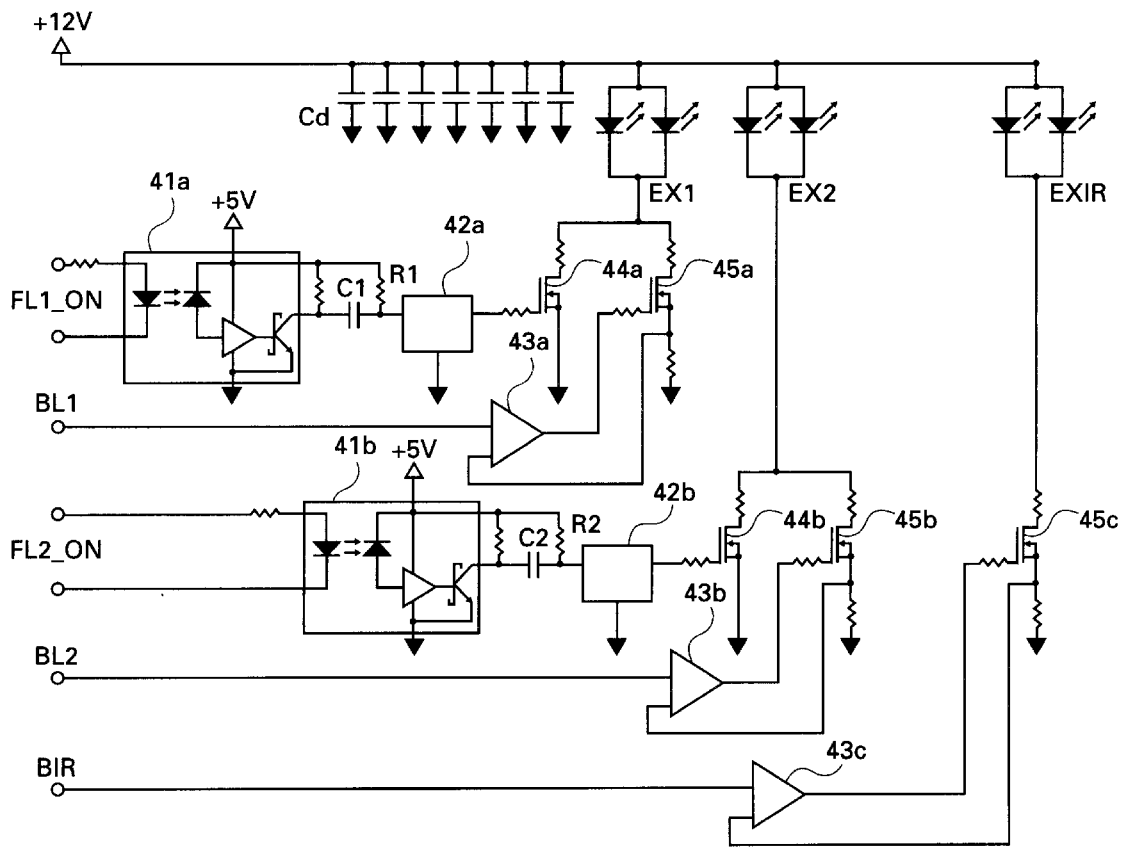
FIG. 4 is a schematic block diagram of a flasher circuit of the MPF shown in FIG. 1.

A schematic block diagram of the flasher circuit 3 is shown in FIG. 4. Each of the gated FL_ON signals (FL1_ON, FL2_ON, FLi_ON; only two of the gated FL_ON signals shown in FIG. 4) from the flash timer circuit 2 is isolated by a corresponding optoisolator 41a, 41b, etc. (e.g., HCPL2631 from Hewlett Packard; only two optoisolators are shown in FIG. 4). Optoisolators 41a, 41b, etc. are used to increase noise immunity between the flasher circuit 3 and the rest of the instrument.

The optoisolator 41a is capacitively coupled via a capacitor C1 and a resistor R1 to a driver 42a (e.g., TC4421CAT from Telecom Semiconductors), which in turn controls the MOSFET transistor 44a (e.g., NDP7060 from National). During the flash, up to a 30 Amp current is forced through the LED bank EX1. The energy required to sustain such a high current is stored in a bank of discharge capacitors Cd (e.g., CE-HFQ type from Panasonic).

The same circuit arrangement is used for LED bank EX2 and signal FL2_ON using corresponding components 41b, 42b, 44b and 45b. Likewise, this arrangement can also used for any of the other LED banks EXi and the corresponding FLi_ON signals.

To achieve the range of optical power required for operation of MPF, the LEDs are driven with up to 20 times their nominal current. This requires limiting the duty cycle (the ratio of Flash_ON/Flash_OFF signal) to less than 5%. The capacitive coupling C1-R1 provides an automatic shut-off of the driver 42a when the length of the Flash_ON signal, for example, exceeds 40 μs, thus preventing the LED's from accidental damage.

To provide background dc illumination with a controlled irradiance level, a background light control circuit, employing amplifier 43a (e.g., OPA2107 from Analog Devices) and MOSFET transistor 45a (e.g., NDP7060 from National) is used. Analog signal BL1, generated by D/A$_1$ converter 4 (e.g., DAC8413 FP from Analog Devices, shown in FIG. 2) controls the current source 43a–45a, thus determining the background illumination level from LED bank EX1. A similar circuit arrangement is used to provide background irradiance from the other LED banks, as shown, for example, by signal BL2 and the circuit elements 43b–45b controlling the LED bank EX2.

A similar circuit can be used to control the level of background infrared illumination by controlling the current flowing through the infrared LEDs (e.g., QDDH73520 from Quantum Devices), as shown, for example, by the LED EXIR controlled by current from the amplifier 43i and the transistor 45i, and responsive to a signal BIR.

Multispectral LED Flasher

To achieve the spectral control of the excitation light in a range of 440 to 540 nm, several LED banks (EX1, EX2, . . . , EXi), each composed of LEDs with different spectral output, are switched ON selectively, or in combination. For example, a selection of LEDs available from Nichia Chemical Industries, with varying spectral output, is presented in Table 1.

TABLE 1

| LED type | Dominant Wavelength (nm) | Half Width range (nm) |
| --- | --- | --- |
| NLPB 300 | 450 | 420 to 480 |
| NSBP 300V | 460 | 445 to 475 |
| NSPB 300X | 475 | 460 to 490 |
| NSPB 300Y | 485 | 470 to 500 |
| NSPE 300C | 495 | 480 to 510 |
| NSPG 300F | 510 | 490 to 530 |
| NSPG 300H | 535 | 525 to 555 |

To eliminate excitation light at wavelength above 650 nm, light from the blue-green LEDs is optionally filtered by a 1 to 3 mm thick glass filter (e.g., BG39 from Shott). At chlorophyll concentration above 10 μg/l and when using the NSPB 300 LED's, the excitation filter is not required because of a high fluorescence signal, and a very small contribution of the red light in these LEDs.

3. Optical Configuration of the MPF

The optical configuration of an excitation source, a sample chamber, and the excitation/emission optics depends on a particular application of the MPF. For example, FIGS. 5A–5J which show several different embodiments of the MPF for measuring photosynthetic parameters in different applications.

Figure 5A:
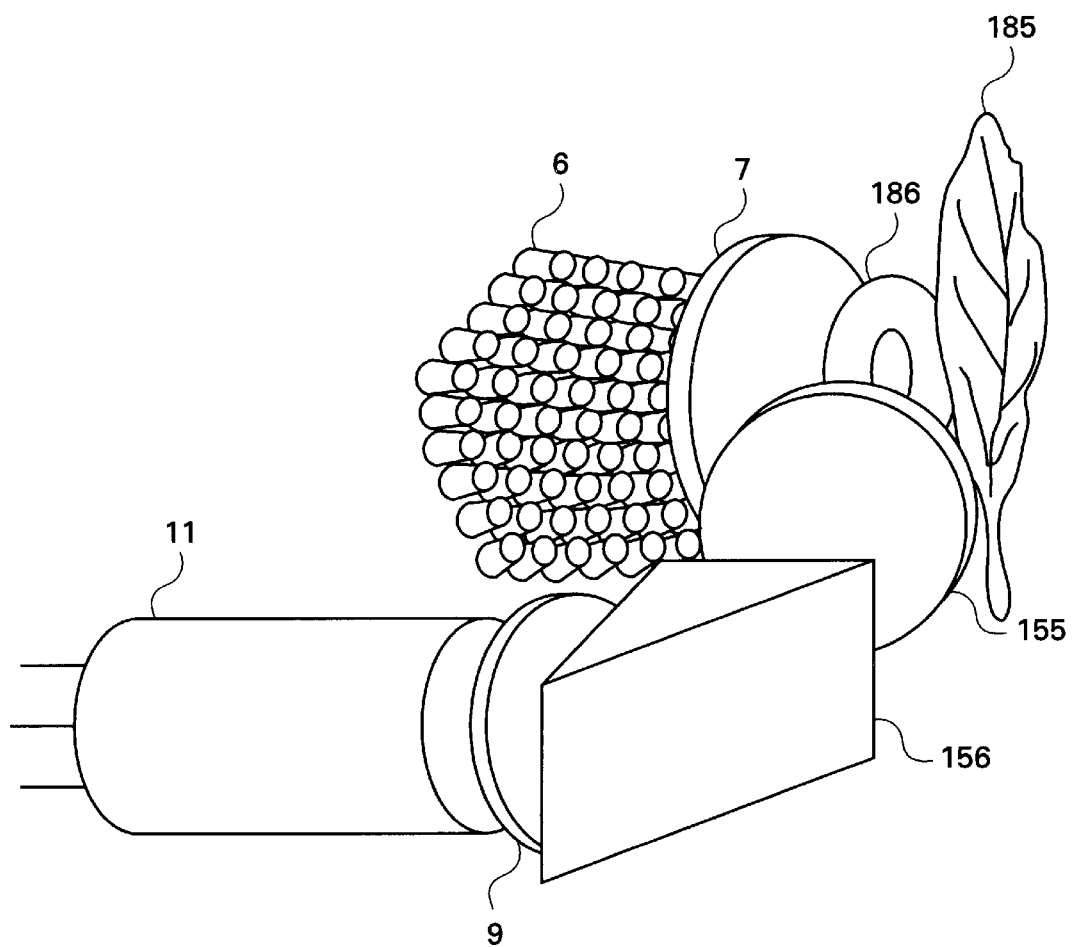
FIGS. 5A–5J illustrate different embodiments of the MPF suitable for various applications of the MPF according to the invention.
Figure 5B:
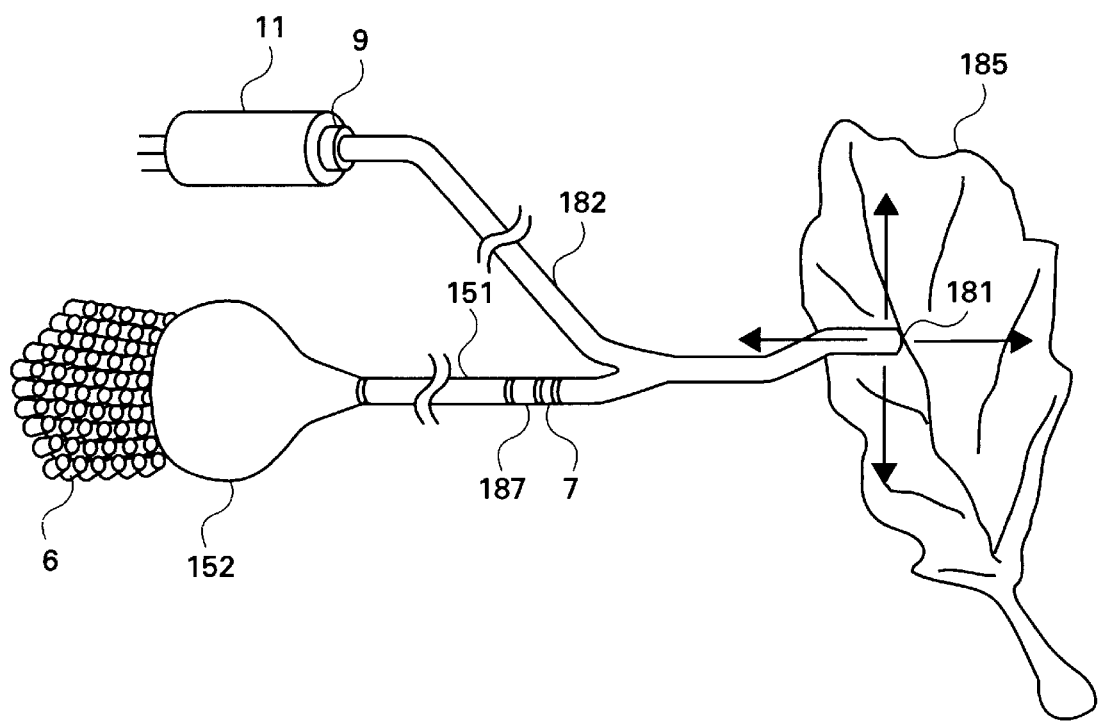
Figure 5C:
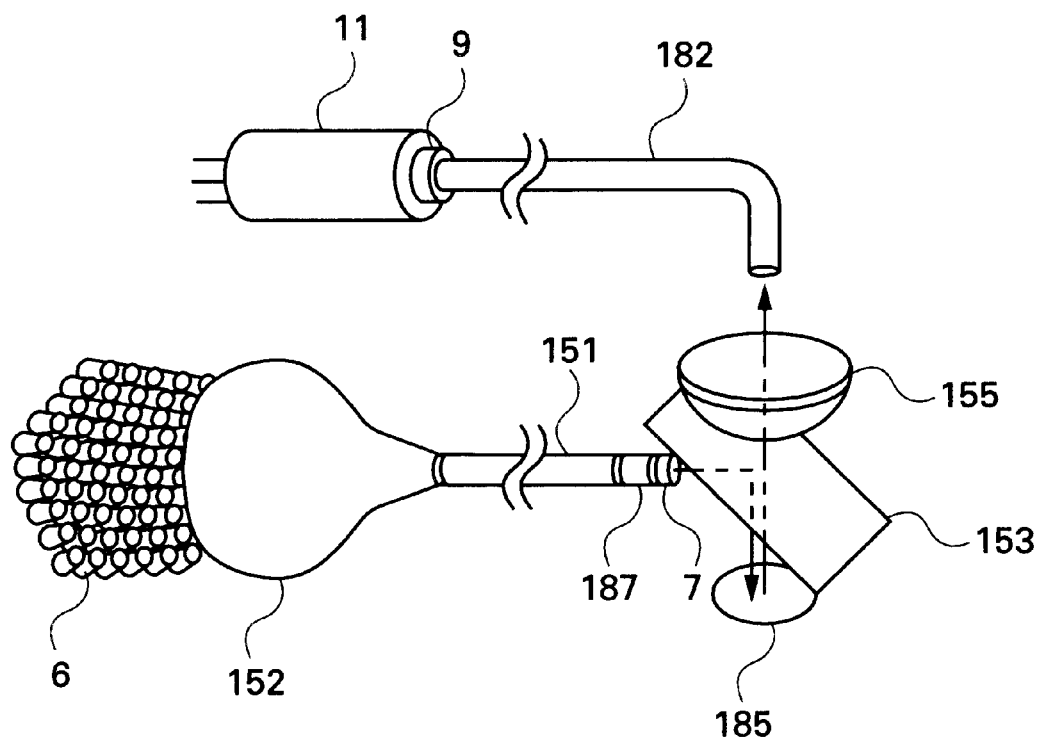
Figure 5D:
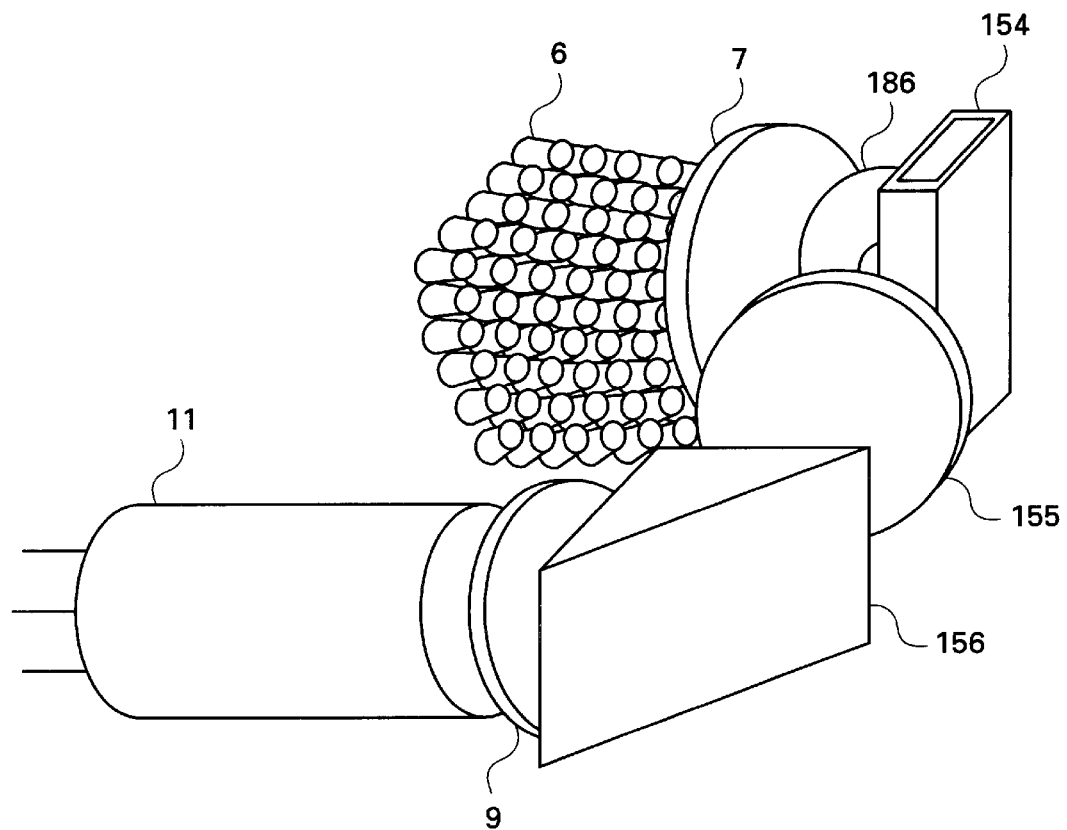
Figure 5E:
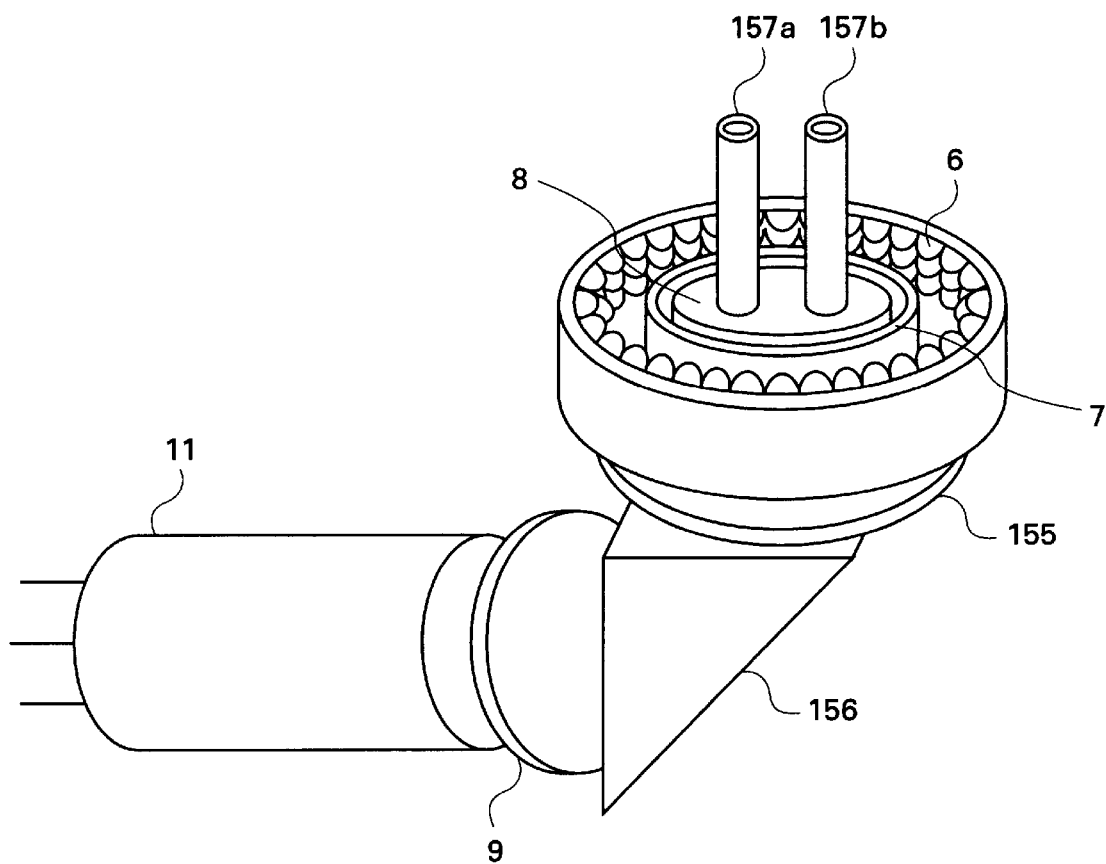
Figure 5F:
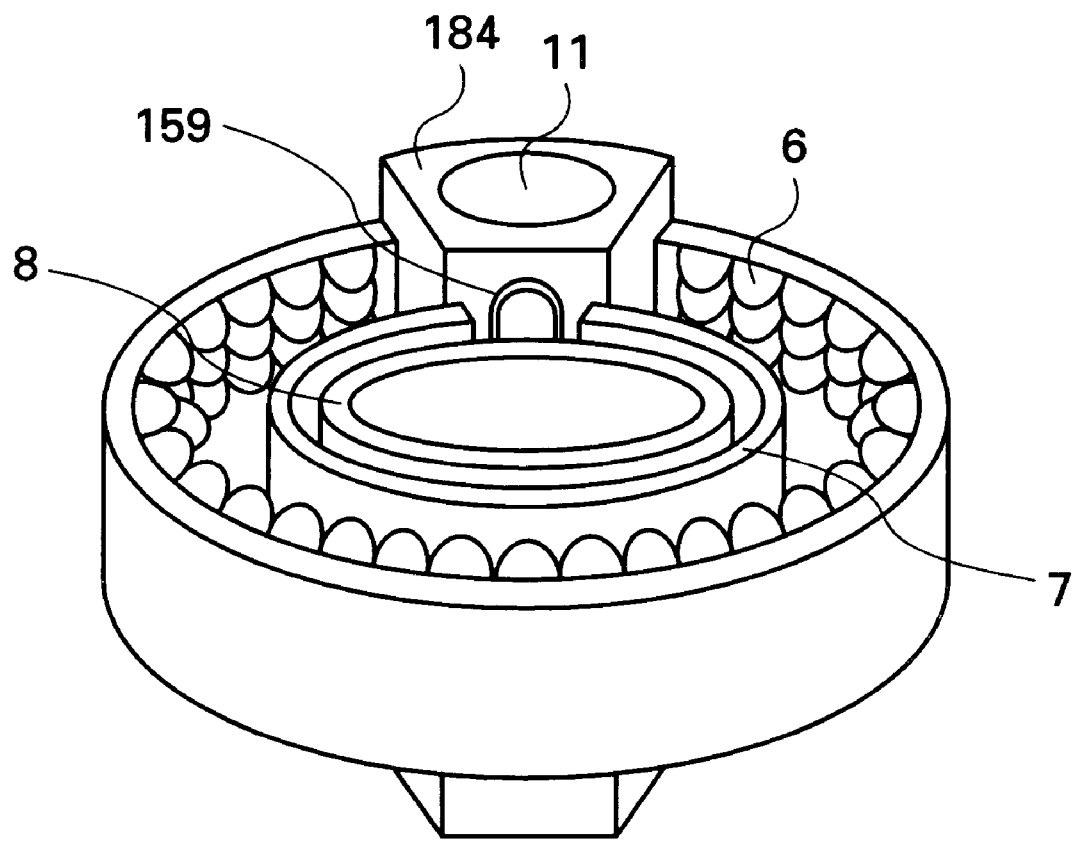
Figure 5G:
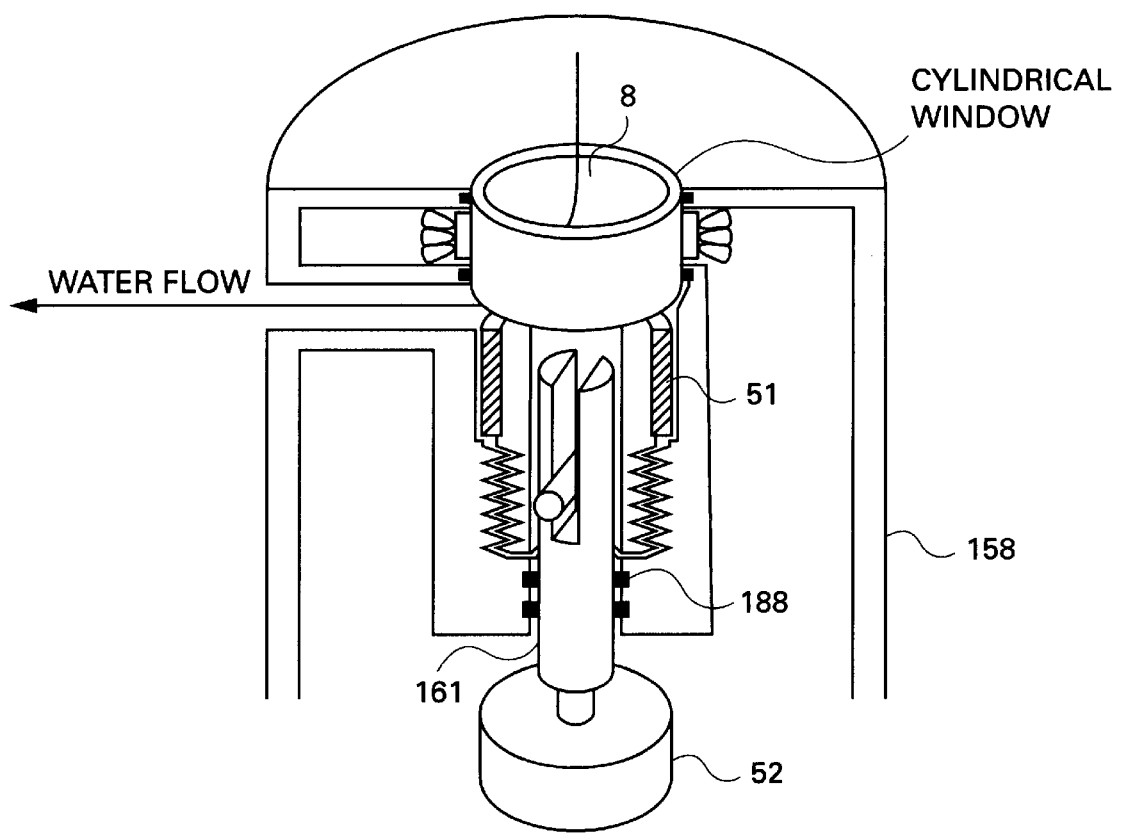
Figure 5H:
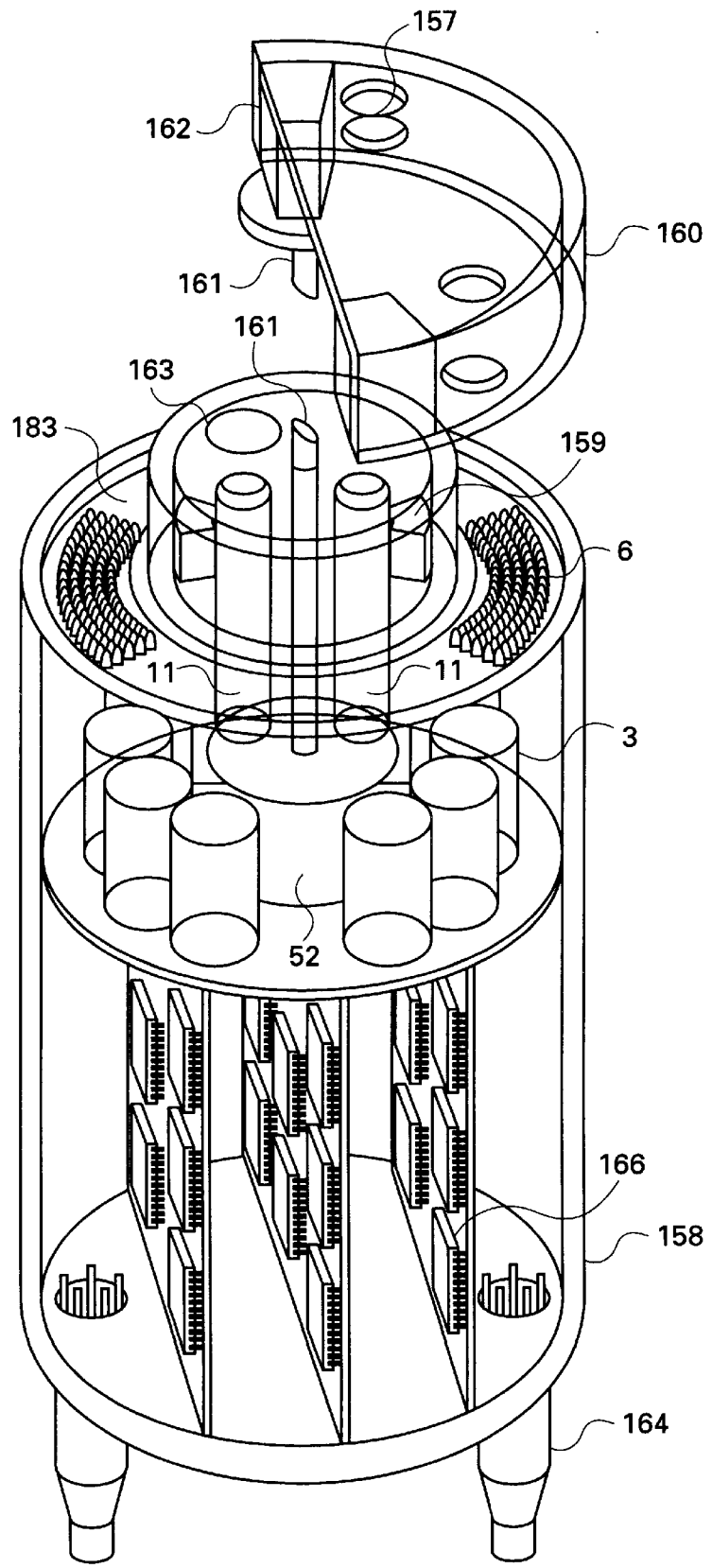
Figure 5I:
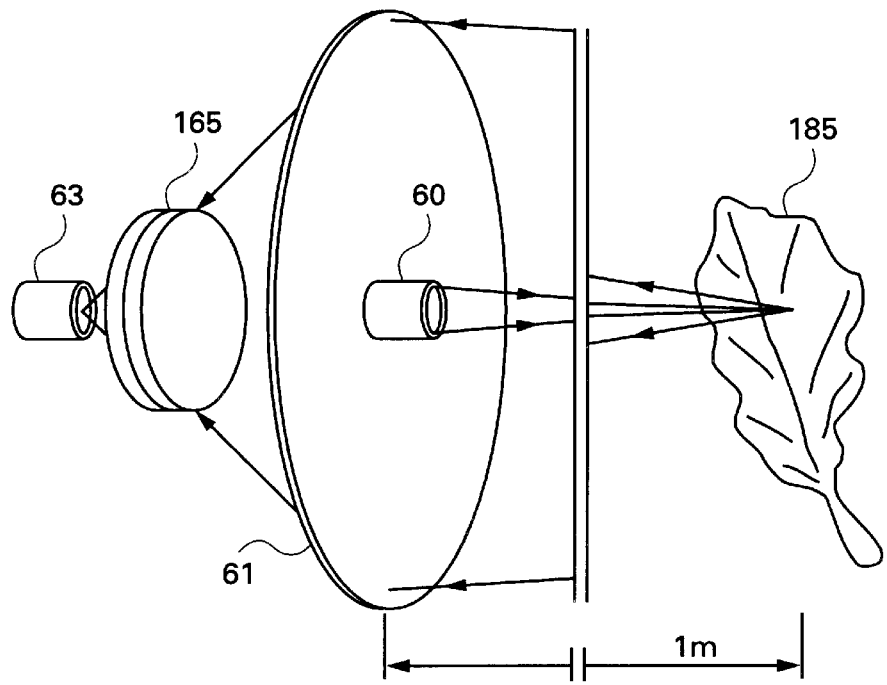
Figure 5J:
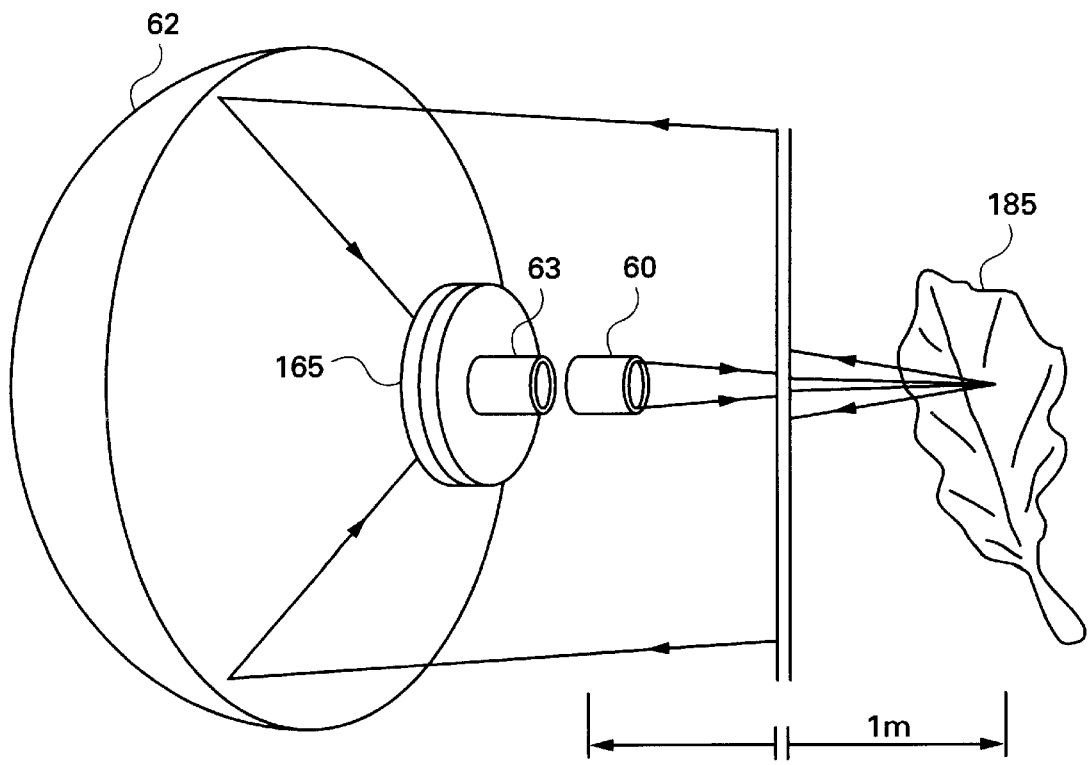

These embodiments can be summarized as follows:

(i) FIG. 5A shows an embodiment of the MPF optics that utilizes a hemispherical configuration of a multispectral LED flasher as an excitation source to measure photosynthetic parameters in leaves;

(ii) FIG. 5B shows an embodiment that uses a tapered fiber rod for concentrating the excitation energy into a bifurcated fiberoptic light guide;

(iii) FIG. 5C shows an embodiment of the MPF optics that uses a tapered fiber rod for concentrating the excitation energy together with a dichroic mirror for separating the excitation light from the emission light;

(iv) FIG. 5D shows an embodiment, similar to FIG. 5A, suitable for measuring photosynthetic parameters in aquatic phytoplankton samples, such as a sample placed in a sample cuvette;

(v) FIG. 5E is an embodiment of the MPF optics that uses a cylindrical configuration of a multispectral LED flasher as an excitation source to measure photosynthetic parameters in aquatic phytoplankton samples where the fluorescence signal is detected from the bottom of the sample chamber;

(vi) FIG. 5F is another embodiment of the MPF optics that uses a cylindrical configuration of a multispectral LED flasher that detects the fluorescence signal from a side of the sample chamber;

(vii) FIG. 5G is an embodiment of a self-cleaning sample chamber that is particularly suited for an application requiring unattended measurements of photosynthetic parameters in, for example, aquatic phytoplankton samples;

(viii) FIG. 5H is a schematic view of an embodiment of a submersible MPF, having two self-cleaning chambers, that is suitable for in situ measurements of photosynthetic parameter in, for example, aquatic phytoplankton samples; and (ix) FIGS. 5I and 5J show two embodiments of MPF optics that use a semiconductor laser diode 60 as an excitation source and are especially suitable for remote sensing and measurement of photosynthetic parameters with the MPF placed at a distance, for example, of about 1–10 m from a sample.

Each of these embodiments are discussed in further detail herein. It should be noted that the reference numbers of the components shown in FIGS. 5A–5J correspond to the reference numbers of the corresponding components shown in schematic block diagram of FIG. 2.

In higher plants application, where fluorescence signal from the plant green tissue (leaves or needles) is measured, the excitation light is delivered to a leaf sample 185 directly as illustrated in FIG. 5A, or via a flexible or rigid fiber-optic guide 151 as illustrated in FIG. 5B.

FIG. 5A shows a multi-spectral LED flasher 6 delivering excitation light to a leaf sample 185 through an excitation filter 7 and an iris 186 that directs the light to the leaf sample 185. The emitted fluorescent light is concentrated by an emission condenser lens 155, and the emission pathway is bent 90 degrees by a prism 156 to ensure a compact design of the excitation/emission optics. The emitted light is then filtered by an emission filter 9 before being detected by a fluorescence detector 11. Therefore, the excitation filter 7, the iris 186, the condenser lens 155, the prism 156, and the emission filter 9 comprise one embodiment of the excitation/emission optics that serves to guide both the excitation light to the sample 185 and emitted fluorescent light away from the sample 185.

FIG. 5B shows another embodiment of the MPF, in which a suitable emission fiber 182 is used to guide the emitted fluorescent light from the sample 185 to the fluorescence detector 11 through an emission filter 9. To increase the optical power density (photon flux), a tapered fiber rod 152 (e.g., PN25255 from Shott) is used in sequence with a GRIN lens 187. An excitation/emission probe 181 is used to guide both the excitation light to the sample and the emitted fluorescent light away from the sample.

The emitted fluorescent light can be detected at a 90 degree angle to the excitation light, as shown in FIG. 5A, or from the face of the leaf sample 185 as shown in FIG. 5B. μs shown in FIG. 5B, a suitable excitation/emission probe 181 may also be used for this purpose. In some applications, as illustrated in FIG. 5C, the excitation light may be bent 90 degree by a dichroic mirror 153 (e.g., CR-500 from Corion), which is transparent for the emitted radiation. The excitation light also passes through a GRIN lens 187.

As shown in FIG. 5D, for aquatic applications, the excitation light is delivered to a standard fluorescence cuvette 154 containing, for example, an algae suspension, and the emitted light is observed at a 90 degree angle as shown in FIG. 5D. The emission light is concentrated by an emission condenser lens 155, and the emission pathway is bent by 90 degree using a prism 156 to ensure a compact design of the excitation/emission optics.

In a laboratory/benchtop application, the most successful design of the excitation/emission optics, as illustrated in FIG. 5E, is based on a cylindrical configuration of the multi-LED flasher 6, cylindrical excitation filter 7, and cylindrical sample chamber 8. The cylindrical excitation filter 7 can be custom designed as two pieces of semi-cylindrical optical glass (e.g., 3 mm thick BG39 glass) by one skilled in the art. The sample chamber 8 is made using a high optical quality cylindrical scattering cells (e.g., T-76 from NSG Precision Cells). The cylindrical configuration allows efficient concentration of the optical energy from a multi-LED flasher 6 within a relatively small volume. Moreover, the curvature of the cylindrical surface of the sample cell 8 collimates the excitation beam from individual LEDs, allowing an uniform illumination field within the sample chamber 8. The cylindrical sample cell 8 can be equipped with two ports, an IN port 157a and an OUT port 157b, that allow continuous fluorescence measurements in a flow-through mode. In this configuration, the emission light is collected from the bottom of the sample cell 8, and then bent 90 degrees by a prism 156 to achieve a compact design of the excitation/emission optics.

In the configuration in FIG. 5F, the emitted fluorescence light is also collected from the side of the sample chamber 8, through an emission window 159 that opens into a housing 184 for a photomultiplier tube 11 or other suitable fluorescence detector. This approach allows a design of a self-cleaning sample chamber 8. In the standard, flow-through operation, the sample chamber or cell 8 must be periodically cleaned every 6–8 hours to prevent accumulation of the suspended material on the internal walls of the sample cell 8.

For applications requiring autonomous operation in the flow-through mode (several weeks of the stand-alone operation during a trans-oceanic transect on oceanographic vessel, or continuous monitoring of phytoplankton cultures), a self-cleaning cuvette or sample cell 8, as shown in FIG. 5G, can be used. The self-cleaning sample cell or cuvette 8 is housed in a watertight housing 158 and uses a cylindrical brush 51, whose rotation and translation movements are controlled by a stepper motor 52 through a shaft 161 extending into the sample cell 8. An O-ring seal 188 forms an additional seal for the shaft 161 that extends into the sample cell 8. At arbitrary or pre-programmed time intervals the stepper motor 52 is activated, and the brush 51 is forced into and from the sample chamber 8 in a rotation-translation motion, to clean the sample cell 8.

In a submersible application, as shown, for example, in FIG. 5H, a watertight housing 158, made of aluminum, stainless steel, or preferably titanium, contains the electronics 166, flasher circuit 3, excitation source 6, and fluorescence detector 11. A TATTLETALE model 8 from Onset Computer can be used as the controller 1 (not shown in the Figure). The instrument is equipped with two excitation/emission channels, one of which is used to measure photosynthetic parameters under ambient irradiance, and the other to measure the photosynthetic parameters in the darkness.

The multi-spectral LED flashers 6 are arranged in a semi-radial configuration. The excitation light, after being filtered by excitation filter 7 (not shown in the Figure), leaves the instrument via optical emission window 159, preferably made of fused silica. The fluorescence emission signal is observed at 90 degree angle via the emission window 159 of cylindrical shape made of fused silica. After being filtered by a set of emission filters 9 (e.g., RG 665 from Shott and A397-2883 from Corion—not shown in the Figure), the fluorescence signal is detected by a pair of photomultipliers 11 (e.g., R4457P from Hamamatsu), described further herein. The dark sample chamber 8 is covered by an opaque cap 160 made of black plastic (Acetron or Delrin). The cap 160 is equipped with several IN/OUT ports 157, allowing water flow through the dark chamber 8 when the instrument is operating in a profiling mode.

In a situation where optical windows 159 are to be periodically cleaned (as in long-term moored applications), the opaque cap 160 is mounted on a rotating shaft 161 powered by a stepper motor 52, and is equipped with two sets of window wipers 162. When actuated, the cap 160 rotates, cleaning the surfaces of both the emission windows 159 and the excitation window 183. Optionally, the window wipers 162 can be equipped with containers (not shown) holding anti-fouling agent, allowed to diffuse through the cleaning surfaces of the wipers 162 during their movement to enhance the cleaning action of the wipers 162.

The submersible instrument is also equipped with a Photosynthetic Active Radiation (PAR) sensor 163, which can either be designed by one skilled in the art, or purchased commercially, for example, from Licor or Biospherical Instruments. The submersible MPF can be equipped with a signal conditioning circuit allowing direct interfacing with a pressure sensor, for example, model SBE-29 from Sea Bird, and a temperature sensor, for example, model SBE-3 from Sea Bird, via a set of underwater connectors 164 at the bottom of instrument. Optionally, the instrument may be equipped with its own pressure and temperature sensors.

FIGS. 5I and 5J show two embodiments of the MPF that use a semiconductor laser diode 60 as an excitation source, and are especially suitable for remote sensing and measuring of photosynthetic parameters with the MPF placed at a distance from a sample 185. The embodiment shown in FIG. 5I collects the fluorescent light using a large diameter Fresnel lens 61 whereas the embodiment of FIG. 5J uses a concave mirror 62.

Commercially available laser diodes 60 operating at a wavelength of, for example, between about 650–670 nm can be used as the excitation source for the MPF fluorometer. A high degree of collimation and coherence of the laser light allows directing the excitation beam at remote targets, and, thereby, allowing the remote measurement of photosynthetic parameters using MPF protocols at a distance of, for example, between about 1–10 m.

In the embodiments shown in FIGS. 5I and 5J, the laser diodes 60 are driven using flasher circuitry (not shown), such as that described with reference to Figure A4, with a resistor-limited current of 35 mA and producing about 5 mW of optical power. The laser light is concentrated at a 1mm spot at a distance of 1 m.

In the embodiment shown in FIG. 5I, the fluorescence light is collected by a large-diameter, short-focal length Fresnel lens 61 (e.g, A32,953 from Edmund Scientific). In the embodiment shown in FIG. 5J, the fluorescence light is collected by a concave mirror 62 (e.g., A32,084 from Edmund Scientific). Other embodiments for collecting light are also possible, such as, for example, a wide field telescope can also be used to collect fluorescence light from remote targets.

After collection, the fluorescence light is filtered by a set of two long-pass emission filters 165 (RG 695 from Shott) and detected by a fluorescence detector such as an avalanche photodiode 63 (C5460 from Hamamatsu). Alternatively, the fluorescence light can be transferred to a photomultiplier based detector (e.g., R2066 from Hamamatsu) using a light guide. The laser diode 60 is operated to generate flashlets of duration controlled between 1.5 $\mu$s to cw (continuous mode). Commercially available pulse drivers can be used to decrease the duration of a flashlet below 1 $\mu$s.

When operated with a bias current below the lasing threshold level, laser diodes 60 produce noncoherent light with an intensity proportional to the bias current. This feature can be used to generate a continuous background irradiance in a way similar to that for the LED-based flashers 6.

Figure 6:
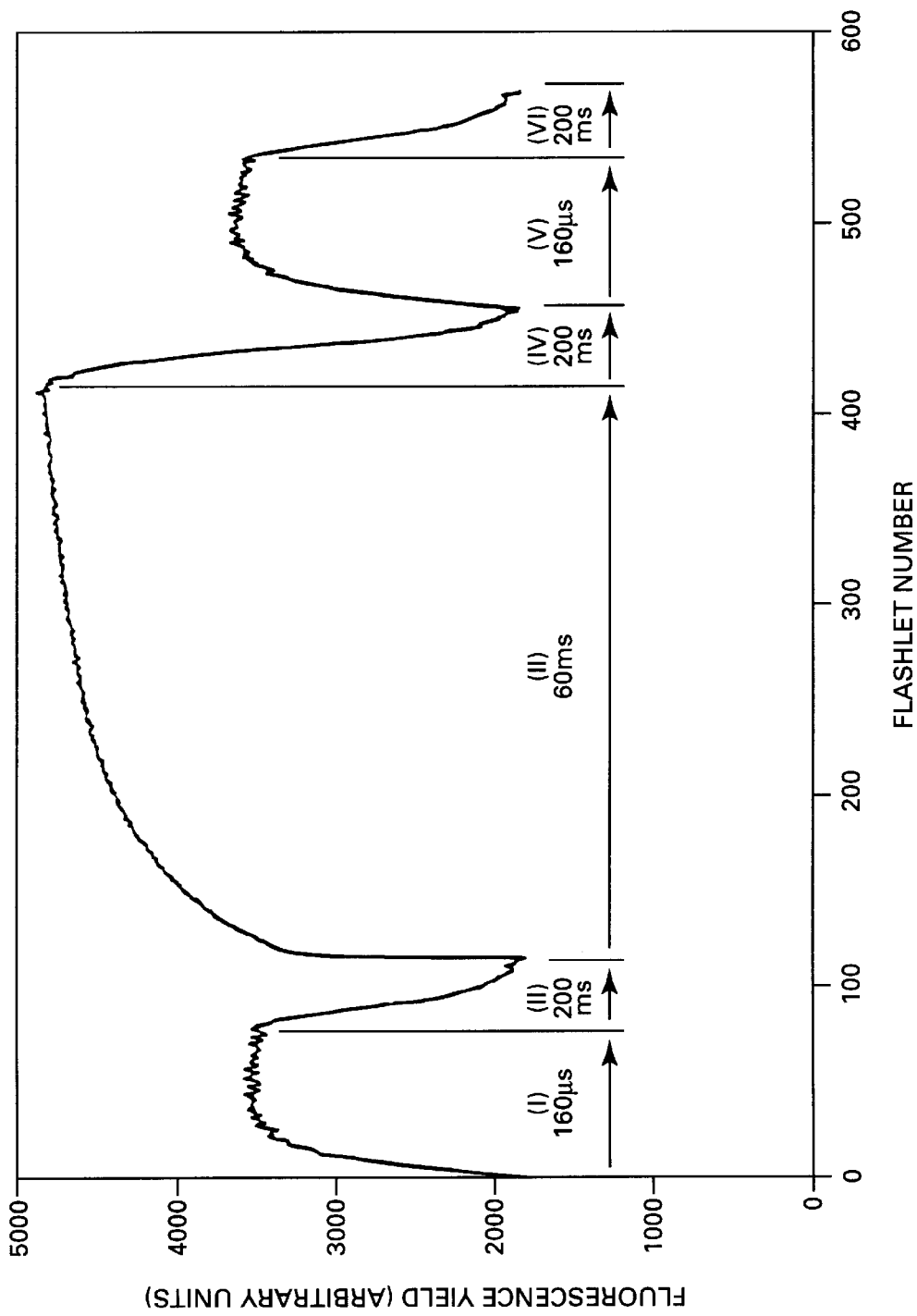
FIG. 6 is a graphical illustration of the fluorescence transients from a maple leaf obtained from a laser-diode based MPF.

FIG. 6 shows the fluorescence transients from a maple leaf acquired with a laser-diode based MPF. Phase I and IV of the M Protocol, described further herein, are produced using 80 flashlets of 1.5 $\mu$s duration and 2 $\mu$s time interval. Phase III is produced using 300 flashlets of 5 $\mu$s duration and 200 $\mu$s time interval. Phases II, IV, and VI is produced using 40 flashlets 2 $\mu$s duration, with a time interval exponentially increasing from 50 $\mu$s to 30 ms.

Using laser diodes 60 with a power range of 100–500 mW at a 650–670 nm spectral range (e.g., LD 1093, LD 1094 from Power Technology), it is possible to make measurements similar to that in FIG. 6 from a distance of more than 10 m, and, thereby, allow remote measurements of photosynthetic parameters in, for example, a tree canopy.

At present, the laser-based fluorometry is limited by the commercial availability of laser diodes with spectral output in a range of about 650–670 nm. However, experimental laser diodes capable of producing light at wavelengths in a range of 450–500 nm have been developed by Phillips and Nichia Corporation, and are likely to be commercially available within 1997–1998. With these laser diodes, it is expected that the methodology and optical configuration disclosed herein can be used to remotely measure the photosynthetic parameters in terrestrial plant and aquatic environments in the blue-green excitation range.

Emission Filters

For the different embodiments of the MPF discussed above, emission filters 9 can filter the fluorescence light at 680–710 nm by a set of a color long-pass glass filter (e.g., RG 665 from Shott) and a narrow band-pass interference filter (e.g., S10-680-R from Corion). The bandpass wavelength of the interference filter is selected between 680 nm to 690 nm for aquatic (phytoplankton) applications, and at 700 nm to 710 nm for terrestrial plants applications. The filtered emission light is detected by a red-sensitive fluorescence detector. The selection of the detector is dictated by the required sensitivity of the emission channel, defined by the chlorophyll concentration, as discussed in the following subsection.

Photomultiplier-based detectors

For the different embodiments of the MPF discussed above, fluorescence detection in aquatic systems where chlorophyll concentration in the oligotrophic oceans averages 0.1–0.3 $\mu$g/liter, is preferably achieved by using photomultiplier-based detectors 11. Among several commercially available photomultipliers, the Hamamatsu R2066, Hamamatsu R928, and Hamamatsu R4457P photomultipliers were found the most preferable, where the R2066 offered the best signal to noise ratio at low chlorophyll concentration, and R4457P allowed the most compact design of the fluorescence detector. When using the photomultiplier, the detector gain is controlled by varying the photomultiplier high voltage (HV) supply using voltage-controlled HV power supply (C1309-04 from Hamamatsu), controlled via D/A converter (DAC 8413 FP from Analog Devices). At chlorophyll concentrations above 10 $\mu$g/l satisfactory performance was observed with avalanche photodiode (avalanche photodiode module C5460 from Hamamatsu), while in the terrestrial plants application, where chlorophyll concentration is several orders of magnitude higher that in aquatic environment, a Silicon PIN photodiode may be used as a fluorescence detector (S1722 from Hamamatsu).

Figure 7:
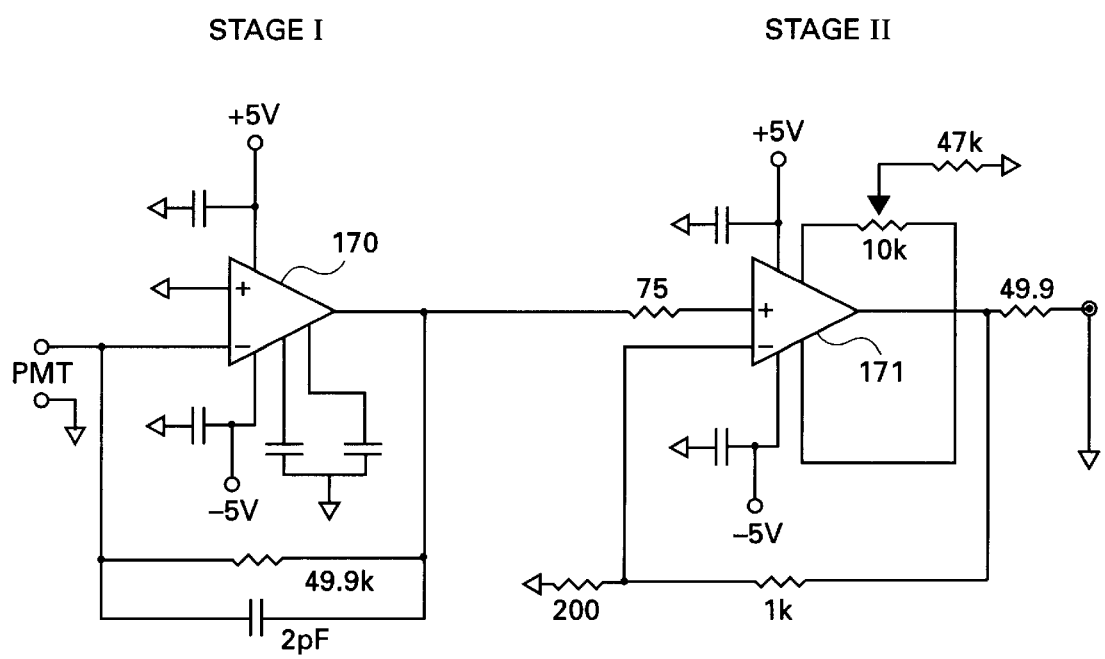
FIG. 7 is a schematic block diagram of a fluorescence channel preamplifier circuit of the MPF shown in FIG. 1.

The photocurrent generated by fluorescence photodetector 11 can be amplified by a fluorescence amplifier 12, as shown in FIG. 2, which can be designed by one skilled in the art. One preferable design of the fluorescence amplifier 12 as a high bandwidth/low noise current/voltage converter and amplifier is shown in FIG. 7 and has two stages. The first stage, based on, for example, an operational amplifier 170, such as, OPA655 from Analog Devices, serves as a current to voltage converter.

The second stage, based on, for example, operational amplifier 171, such as, LT1227 from Linear Technology, serves as a voltage amplifier. Optionally, the fluorescence amplifier 12 can be designed as a load resistor followed by a voltage amplifier.

Where fluorescence measurements are conducted under ambient irradiance, dc (direct current) signal rejection circuit is required to separate the ac signal (fluorescence signal generated in response to the excitation flashlets) and dc signal (red background light present in solar irradiance, and/or fluorescence signal generated in response to background illumination). The dc rejection can be implemented by capacitive coupling between the fluorescence detector 11 and the first stage of the fluorescence amplifier 12, or between first and the second stages of the fluorescence amplifier 12. Both these solutions, however, are susceptible to the noise, and suffer from a baseline drift, requiring additional baseline-restoration circuitry.

Therefore, a more preferred approach, as shown in FIG. 2, is to sample the background signal prior to application of the excitation flashlets using a Sample and Hold (S/H) circuit 15, and to subtract background signal from the fluorescence signal at the subsequent amplification stage using a differential amplifier 16. Using this approach, up to 20:1 rejection of the dc signal was obtained without the degradation of the signal to noise ratio. Following the ac/dc separation and amplification, the fluorescence signal is digitized at 16 MHZ rate with 10 bit resolution, using a flash A/D converter 17 (e.g., SPT7850 available from Signal Processing Technology). The digitized signal is then stored in a fluorescence RAM 18 (e.g., 512k×8 HM628512P-5SL RAM from Hitachi)

FIG. 2 also shows that to accurately measure the intensity of the excitation light, a reference signal is detected using a reference detector 10, such as a silicon PIN photodiode (e.g., S1190 from Hamamatsu). The reference signal is amplified and then digitized using an A/D converter 21 (e.g., SPT7850 available from Signal Processing Technology) and stored in a reference RAM 22 (e.g., HM628512P-5SL from Hitachi) synchronously with the fluorescence signal.

The digitized fluorescence and reference signals are read from the respective RAMs into the Controller 1, as seen in FIG. 2. This operation is performed either following the completion of a whole excitation sequence, or during the excitation protocol if the time interval between flashlets is sufficiently long (reading of the pair of fluorescence/reference data from RAM into the controller takes between 0.125 $\mu$s to 0.8 $\mu$s, depending on the type of I/O operation).

Figure 8A:
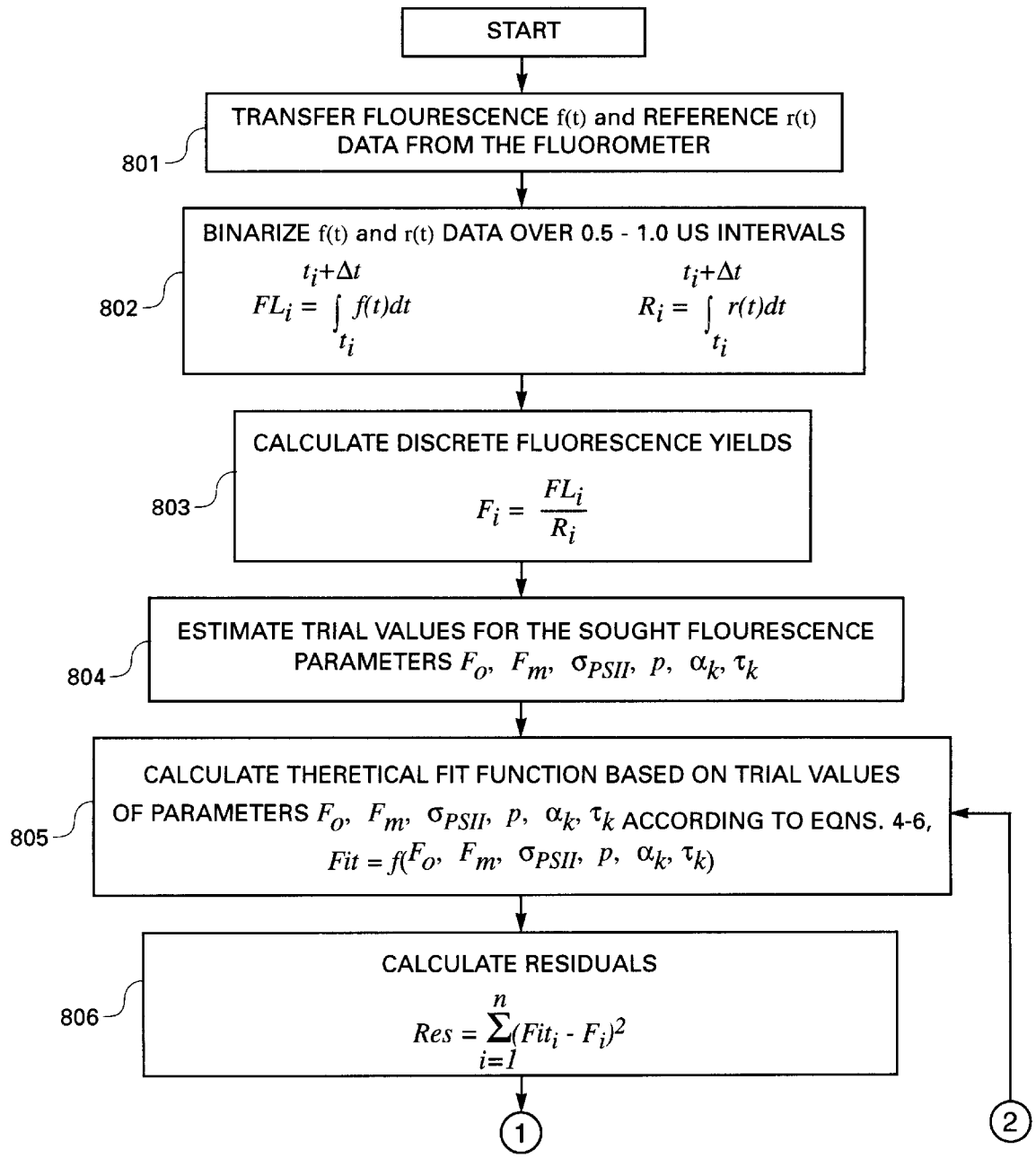
FIGS. 8A and 8B show a flowchart depicting the steps of a data reduction algorithm after fluorescence/reference data is read into a controller.
Figure 8B:
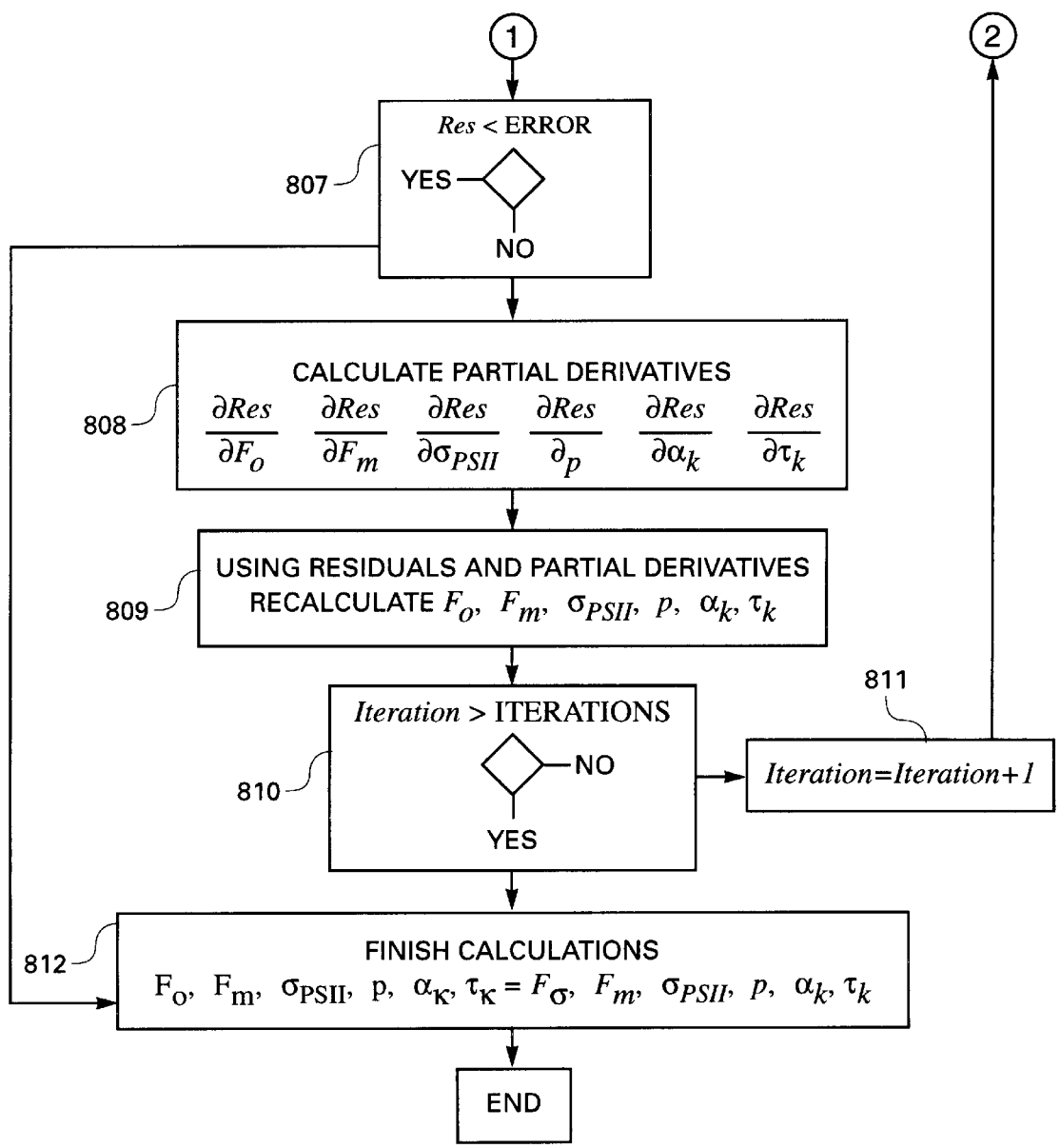

After fluorescence/reference data is read into the controller 1, a data reduction algorithm is initiated. The steps of a typical data reduction algorithm are illustrated in FIGS. 8A and 8B. As shown in these figures, the algorithm consist of binarizing the fluorescence/reference data into 0.5–1.0 $\mu$s long intervals, and the subsequent numerical calculation of the different photosynthetic parameters ($F_0$, $F_m$, $\sigma_{PSII}$, etc.) using standard methods for nonlinear numerical analysis, the steps of which are shown, for example, in FIGS. 8A and 8B.

In step 801, the fluorescence and reference data is transferred from the fluorometer to the control and data processing unit. In step 802, the fluorescence and reference data is binarized over 0.5–1.0 $\mu$s intervals before calculating the discrete fluorescence yields in step 803.

In steps 804–811, the data reduction algorithms estimates the desired fluorescence based photosynthetic parameters by starting with estimate trial values of the photosynthetic parameters in step 804 and then iterating through step 805–811.

In step 805, a theoretical fit function is calculated based on the trial values in accordance with Equations 46 described earlier herein. In step 806 a residual value is calculated corresponding to the differences between the theoretical fit function values and the detected discrete fluorescence yields calculated in step 803.

In step 807, the residual value is compared against an allowable error value. If the residual value is within the allowable error value, the algorithm proceeds to step 812 which finishes the calculations with the values of the photosynthetic parameters used in the latest iteration. If the residual value exceeds the allowable error, the algorithm proceeds to step 808 in which partial derivatives are calculated with respect to the photosynthetic parameters. In step 809, the photosynthetic parameters are recalculated using the residuals and the partial derivatives calculated in step 808.

In step 810, the algorithm checks to determine if the number of iterations exceeds a predetermined maximum number of iterations. If no, the algorithm updates the count of the number of iterations in step 811 and then proceeds to step 805 to execute the next iteration by calculating a theoretical fit function using the photosynthetic parameter values recalculated in step 809. If yes, the algorithm proceeds to step 812 which finishes the calculations with the values of the photosynthetic parameters determined in step 809 of the last iteration.

4. Protocols

According to the invention, at least four novel excitation protocols are provided to measure various photosynthetic parameters of phytoplankton and higher plants including: spectrally-resolved functional absorption cross section of PSII, spectrally-resolved optical absorption cross section of PSII, extent of energy transfer between reaction centers of PSII, $F_0$ (minimal), $F_m$ (maximal) and $F_v$ (variable) components of PSII fluorescence, quantum yield of photosynthesis, photochemical and non-photochemical quenching, size of the plastoquinone (PQ) pool, and the kinetics of reduction/reoxidation at various stages of electron transport from PSII to a terminal electron acceptor. Each of the four experimental protocols will be described in turn.

M-protocol

Figure 9A:
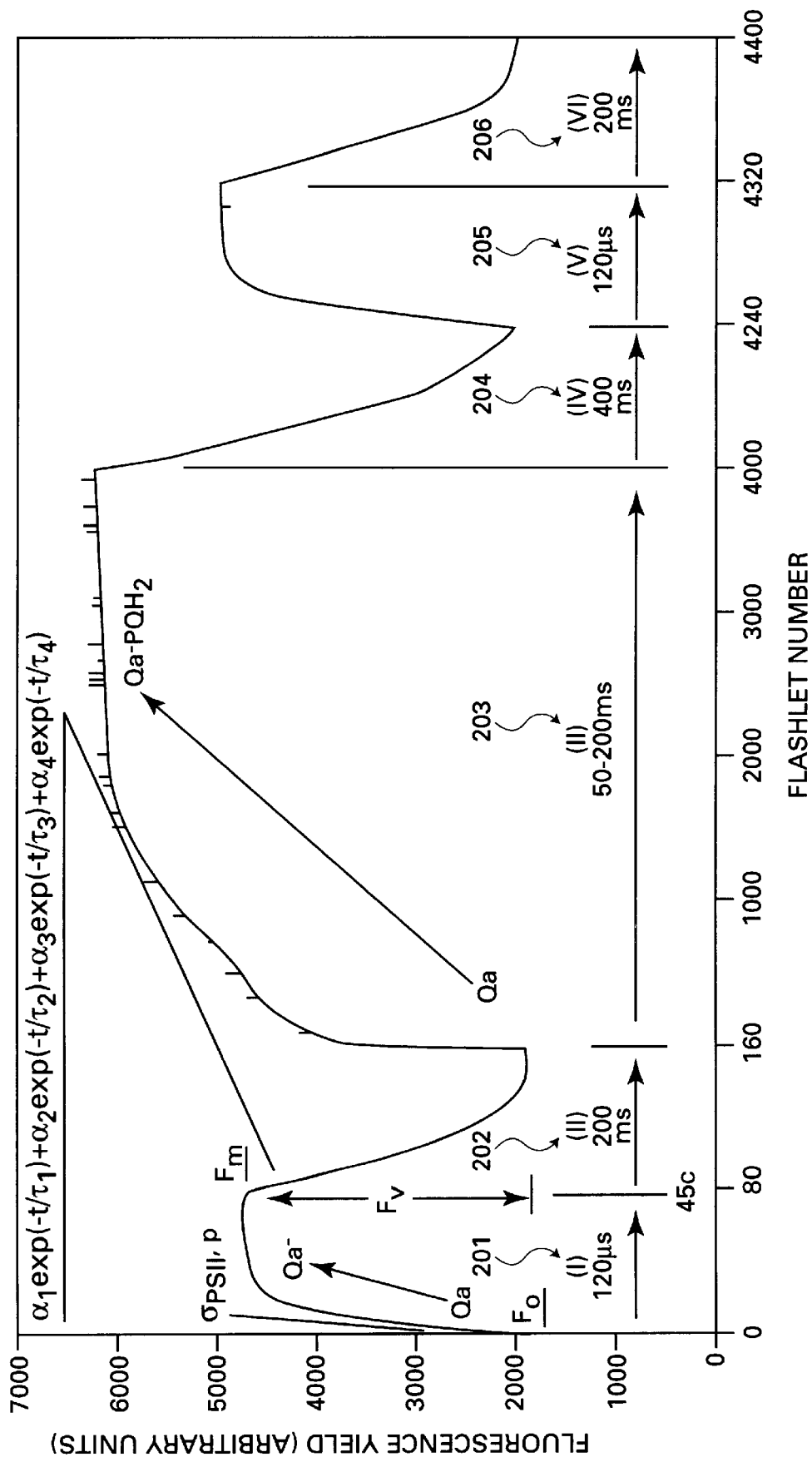
FIGS. 9A–9D are graphical illustrations of the fluorescence yield response generated by the M-protocol, Z-protocol, F-protocol, and feedback protocol, respectively.

M-protocol consists of six sequential phases (Phases I–VI illustrated as the respective reference numbers 201–206 in FIG. 9A). During Phase I, PSII is excited with 60–100 flashlets having high excitation energy and a duration of 0.5–1 $\mu$s, with time intervals between flashlets at 0.5–2 $\mu$s. The excitation results in a fluorescence yield rise from the $F_0$ to $F_m$ level within 40–80 $\mu$s. During this phase, the character of fluorescence saturation profile is mostly controlled by the level of variable fluorescence, $F_v$, by the functional absorption cross section of PSII, $\sigma_{PSII}$, and by the probability of energy transfer between PSII reaction centers, p. By measuring the fluorescence yield in Phase I, the initial portion of the fluorescence transient, which is critical for assessment of the extent of energy transfer between PSII reaction centers, can be resolved, mainly as a result of the higher flashlet rates (0.5 to 2.0 MHz) that is achieved with the MPF according to the invention.

During Phase II, 60–100 flashlets having low excitation energy and a duration of 0.125–0.5 $\mu$s are generated, with time intervals between flashlets exponentially increasing from about 50 $\mu$s to 20 ms. The excitation results in relaxation of the fluorescence yield with the kinetics corresponding to rate of $Qa^-$ reoxidation. The fluorescence transient observed during this phase is fitted to a sum of three or four exponential components, each attributable to a different pathways of $Qa^-$ reoxidation, or stages of electron transport from $Qa^-$ to PQ pool.

During Phase III, 2000–4000 flashlets having a duration of 0.5–4 $\mu$s are generated, with time intervals between flashlets at 20–100 $\mu$s, to reduce PQ pool (PQ $PQH_2$). The electrical power dissipated when generating a 1 $\mu$s long flashlet in the MPF is small, about 0.5 mJ (40 A current at 12 V). By comparison, the electrical power dissipation in the xenon flashlamp of the FRR fluorometer when generating a 1 $\mu$s long flashlet is about 300 times larger.

The character of fluorescence yield changes during Phase III is controlled by $\sigma_{PSII}$, the size of the PQ pool, and by the rates of PQ pool reoxidation. The major pathway of PQ pool reoxidation is the electron transport from PQ pool to Photosystem I. As PQ pool becomes progressively reduced, the fluorescence yield rises above the saturation level reached during Phase I, reflecting changes in the intrinsic fluorescence yield due to prolonged electron occupation of the Qb site in Qa ($\Psi_{Qb}$ factor in Eqn. [1]). Eventually, the fluorescence yield saturates when PQ pool becomes completely reduced.

Phase IV generates about 60–100 flashlets having a duration of 0.125–0.5 $\mu$s, at time intervals exponentially increasing from 50 $\mu$s to 40 ms. Phase IV causes a relaxation of the fluorescence yield with the kinetics corresponding to electron transport from PQ pool to PSI and to terminal electron acceptor.

Phases V and VI are identical to Phases I and II, respectively, and are performed to examine whether the transient reduction of PQ pool have modified the intrinsic fluorescence yield, $\sigma_{PSII}$, or probability of energy transfer between PSII reaction centers.

The excitation sequence in each of Phases I to VI (number of flashlets, flashlet length, and time interval between flashlets) is software programmable, allowing flexible design of the M-protocol.

In Phases I and V, all PSII reaction centers are saturated or reduced within 40–80 $\mu$s, thus inducing a single photochemical electron turnover. The condition of a single electron turnover is required for proper assessment of functional absorption cross section and the extent of energy transfer between PSII reaction centers. To satisfy this condition, the required photon flux density must be higher than 60,000 quanta/RCII/sec. Assuming a minimal value for the functional absorption in a range of 2e–14 $cm^2$, the required quanta flux is about 2e+18 quanta/$cm^2$/sec or 1.27 W/$cm^2$ of optical power at 470 nm. When 100 flashlets are generated during Phases I and V, the flashlet optical energies are in a range near 1.27 $\mu$J/$cm^2$.

In Phases II and VI, the flashlet excitation energy is kept at the same level as in Phases I and V, but the time interval between flashlets increases, resulting in lower average excitation power. During Phases II and VI, the flashlet excitation energy should be as low as possible to avoid self-excitation of PSII. The lower limit is determined by signal-to-noise ratio in the measured fluorescence signal. It is impractical to limit flashlet excitation energies below 0.3 $\mu$J/$cm^2$.

Z-protocol

Figure 9B:
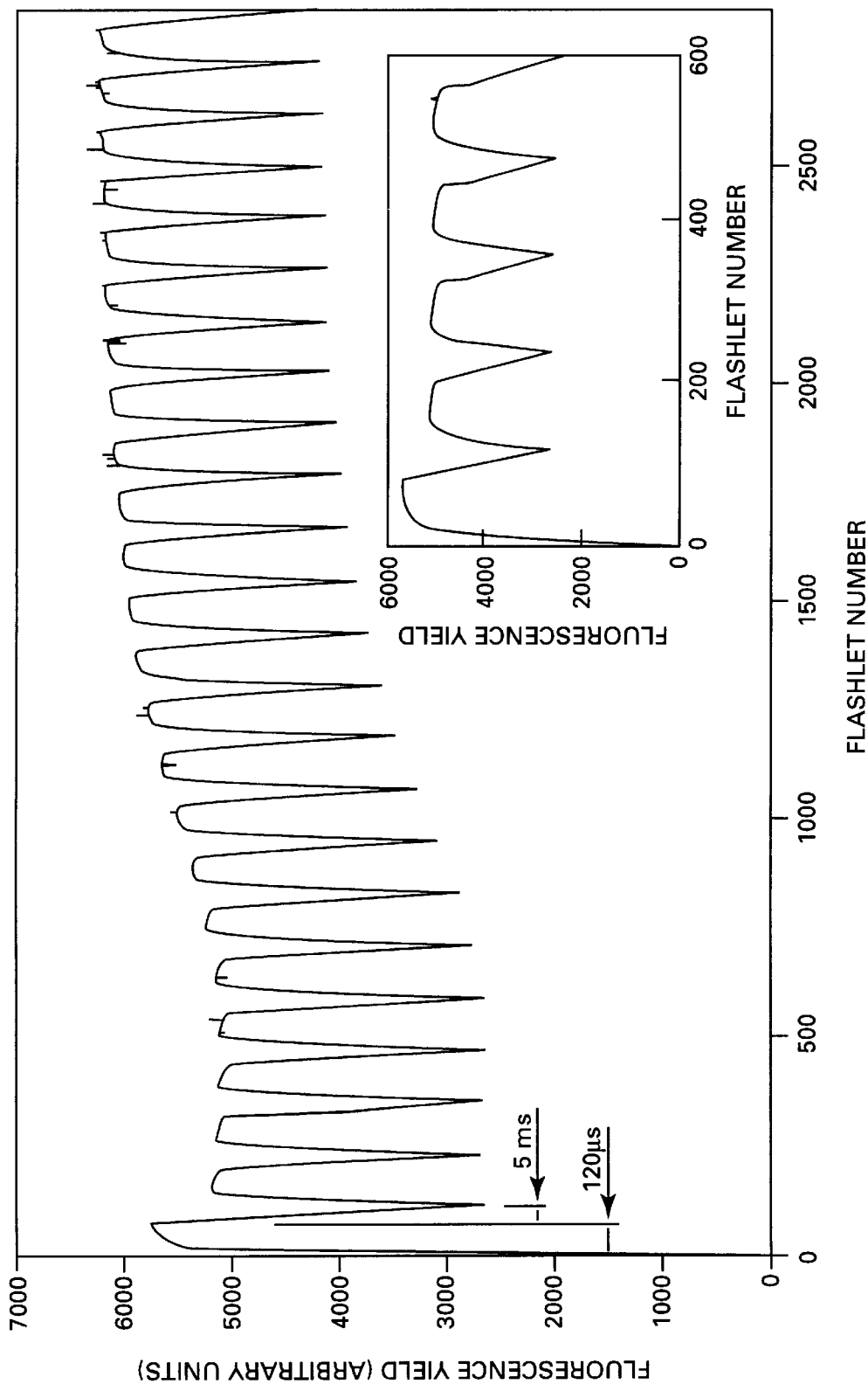

Z-protocol, an example of which is illustrated in FIG. 9B, consists of a series, preferably a series of 15–30, Phase I-II sequences (the first two phases in M-protocol), each consisting of about 40–80 flashlets, with the length of each Phase II duration in a range of 200 $\mu$s to 10 ms.

This protocol provides information about the early stages of electron transport following single-turnover reduction of the first electron acceptor in PSII, allowing examination of the electron transport kinetics at discrete, sequential, one-electron transfers from Qa to PQ pool. As shown in the insert graph of FIG. 9B, this kinetics show a dramatic difference between the first and the consecutive flashlets, followed by more gradual changes as PQ pool becomes progressively reduced.

The fluorescence yield observed during Z-protocol gradually increases, reaching a plateau when PQ pool becomes reduced. Counting the number of electrons transferred to PQ pool prior to reaching this plateau allows estimation of the PQ pool size.

F-protocol

Figure 9C:
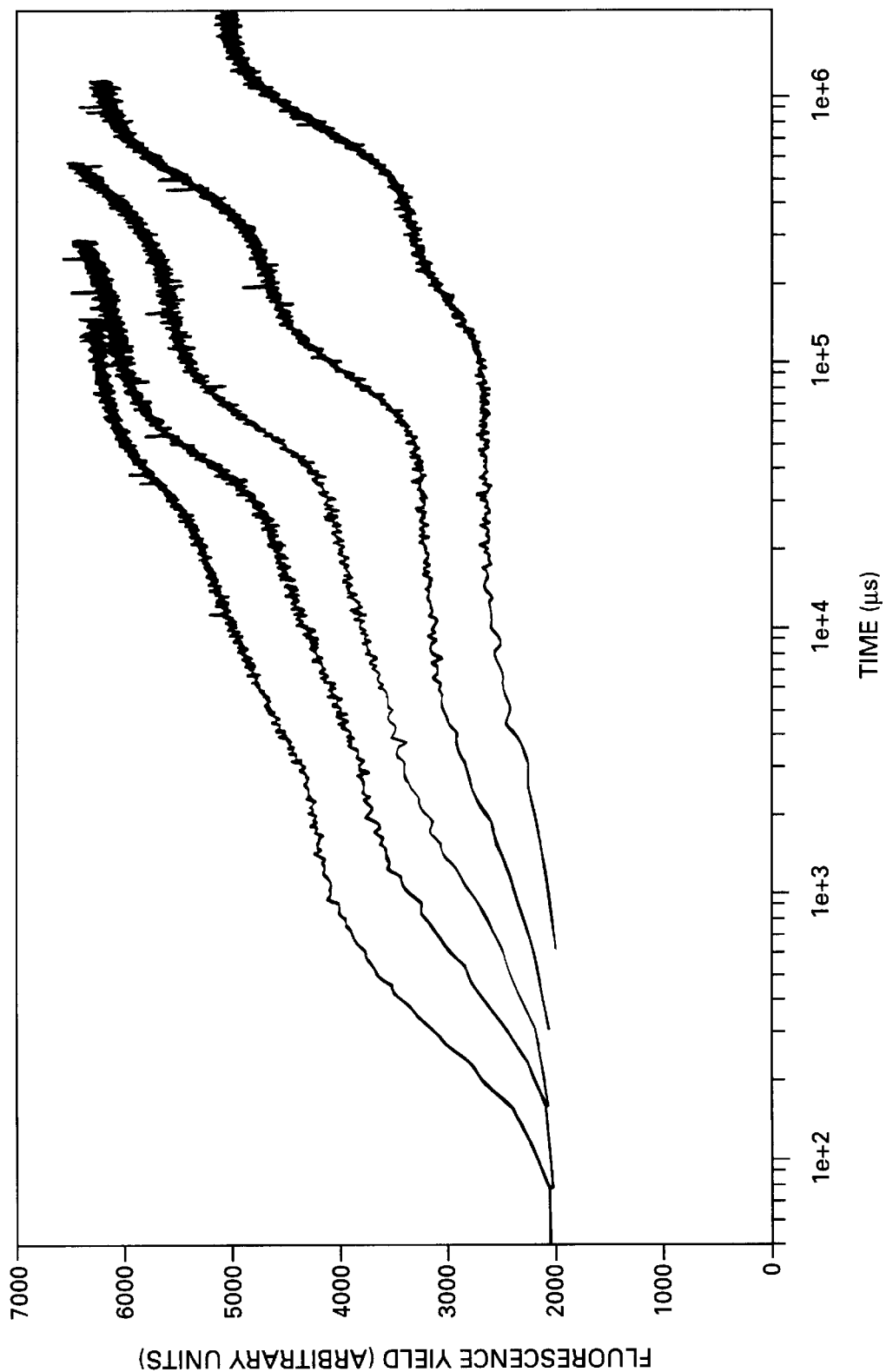

F-protocol, an example of which is illustrated in FIG. 9C, consists of a sequence of 3000–10000 flashlets, each of an individually controlled duration between 0.5 $\mu$s and 4 $\mu$s, and at individually controlled time interval between flashlets, while the flashlets energy is kept constant.

This protocol permits the most flexibility in design of excitation sequence, allowing a thorough investigation of the photosynthetic apparatus. The fluorescence yield changes observed during F-protocol show several phases corresponding to filling and emptying different electron pools within PSII. Expression of these phases, as well as the fluorescence signal attained during these phases is controlled by the excitation energy, functional absorption cross section, and the rates of electron transport between electron carriers within PSII and PSI.

Feedback Protocol

Figure 9D:
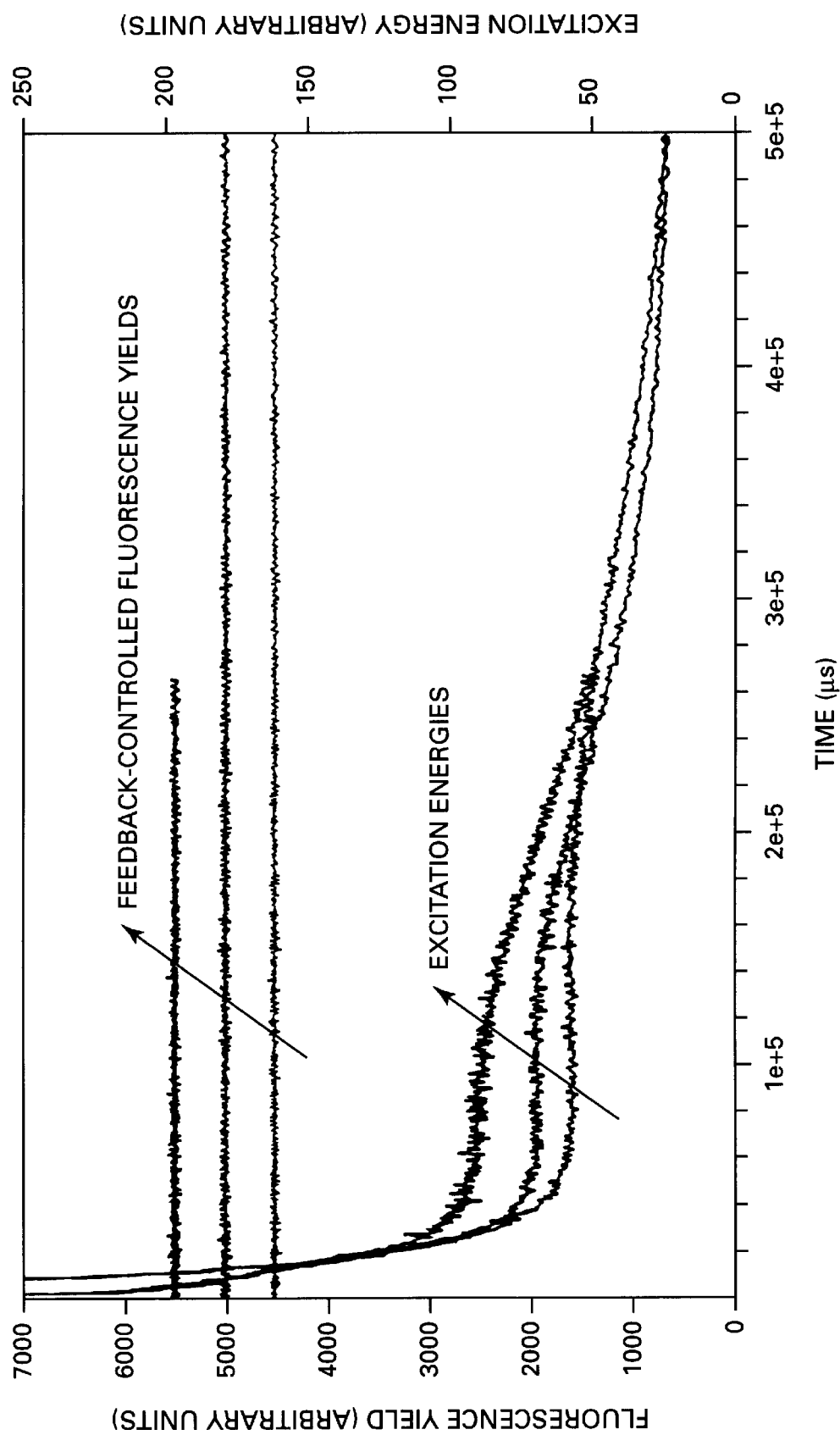

During the feedback protocol, an example of which is illustrated in FIG. 9D, a preset level of fluorescence yield is maintained by continuously adjusting the time interval between excitation flashlets, or by continuously adjusting the energy/length of flashlets. The excitation energy, I(t), required to support a given level of the fluorescence yield (or level of Qa reduction) is proportional to the actual rates of electron transport within PSII. When measured on a dark adapted samples, these rates are maximal at the beginning of the excitation protocol, when most of the electron carriers within PSII are oxidized, and rapidly decrease when the sequential carriers become transiently reduced. The pattern of excitation energy changes during the feedback protocol allows calculation of the reduction/reoxidation rates at various stages of electron transport within PSII.

Alternative Protocols

All of the above described protocols can be further enhanced by simultaneous application of the background light, both in the blue-green spectral region (420 nm<$\lambda$<555 nm), and far red region ($\lambda$>700 nm), allowing selective manipulation of photosynthetic activity within PSII and PSI. The background illumination is possible due to design of the excitation light source employed in MPF, allowing both, the pulsed, and continuous illumination of the sample. Moreover, all these protocols can be performed with different spectral excitation, yielding information about the composition and organization of photosynthetic pigments.

In summary, the M-protocol is used to measure the $F_m$ and $F_0$ components of variable fluorescence, the spectrally resolved functional ($\sigma_{PSII}$) and optical absorption ($a_{PSII}$)

cross sections, and to assess the extent of energy transfer between PSII reaction centers. Phase II and IV of the M protocol are used to assess the kinetics of electron transport from Qa to PQ pool, and from PQ pool to PSI, respectively.

The Z-protocol is used to asses the size of the PQ pool and to evaluate changes in the photosynthetic parameters at different stages of the PQ pool reduction. This information can not be deduced from the M-protocol.

The F-protocol is used to evaluate fluorescence and photosynthetic response to a transient exposure, or to transient changes in the irradiance level. The F-protocol, in contrast to the two previous ones, is usually performed over time scales of seconds or minutes, and is used to evaluate the effects of changing irradiance regime on photosynthetic performance of plants and phytoplankton. Finally, the feedback protocol is used to follow a sequential reduction/reoxidation of electron carriers within PSII and PSI following exposure to light.

In investigating photosynthetic parameters, it is expected that the M-protocol will be the most commonly used. The decision or desire to perform other protocols will depend on a particular question regarding the functioning of the photosynthetic apparatus. These protocols also provide elements of a framework for a design of a "real" protocol, that may be a combination, or a direct sequence of any of the protocols described.

The MPF described herein, according to the invention, provides hardware for performing these protocols, software for design and control over these protocols, and software for analysis of data acquired under any of these protocols and any combination thereof.

To illustrate, the M-protocol may be modified to consist of 2 sequences of Z-protocol, followed immediately by a typical M protocol, then by 4 sequences of Z protocol applied at time intervals of 1, 5, 10, and 20 seconds. Following this, the feedback protocol is selected to be run several times.

Other embodiments of the invention will be apparent to those skilled in the art from a consideration of the specification and practice of the invention disclosed herein. It is intended that the specification be considered as exemplary only, with the true scope and spirit of the invention being indicated by the following claims.

What is claimed is:

1. A method of stimulating and analyzing a fluorescence signal in a sample, the fluorescence signal being measured to analyze parameters of the sample, said method comprising the step of:

(i) exciting the sample with a sequence of flashlets having a duration of about 0.5–1 $\mu$s each and time intervals ranging from about 0.5 $\mu$s to 2.0 $\mu$s, to saturate PSII reaction centers in the sample within about 40–80 $\mu$s.

2. The method recited in claim 1, further comprising the steps of:

measuring an intensity of an emitted light to generate the fluorescence signal; and processing the fluorescence signal to numerically calculate measures of photosynthetic parameters, wherein the photosynthetic parameters include at least one of $F_0$ (minimal) and $F_m$ (maximal) components of PSII fluorescence, spectrally resolved functional ($\sigma_{PSII}$) and absorption ($a_{PSII}$) cross sections, energy transfer between PSII units, kinetics of electron transport between $Q_a$ and PQ pool and between PQ pool and PSI, PQ pool size, and photochemical and non-photochemical quenching.

3. The method recited in claim 1, wherein step (i) of exciting includes exciting the sample with about 60–100 flashlets.

4. The method recited in claim 3, further comprising the step of:

(ii) exciting the sample a second time with about 60–100 flashlets having a duration of about 0.125–0.5 $\mu$s each and time intervals exponentially increased from about 50 $\mu$s to 20 ms.

5. The method recited in claim 4, further comprising the step of:

(iii) exciting the sample a third time with about 2000–4000 flashlets having a duration of about 0.5–4 $\mu$s each and time intervals ranging from about 20 $\mu$s to 100 $\mu$s, to increase the fluorescence yield in the sample above the saturation level reached as a result of the step (i) of exciting.

6. The method recited in claim 5, further comprising the step of:

(iv) exciting the sample a fourth time with about 60–100 flashlets having a duration of about 0.125–0.5 $\mu$s each and time intervals exponentially increased from about 50 $\mu$s to 40 ms.

7. The method recited in claim 6, further comprising the step of:

repeating step (i) and step (ii).

8. The method recited claim 7, wherein each step of exciting includes the step of illuminating the sample with background light in a blue-green spectral region (420 nm<$\lambda$<555 nm).

9. The method as recited claim 7, wherein each step of exciting includes the step of illuminating the sample with background light in a far red region ($\lambda$>700 nm).

10. The method recited in claim 7, wherein each step of exciting includes the step of controlling a spectral output of the flashlets between about 420 nm and about 555 nm.

11. The method recited in claim 7, wherein each step of exciting includes the step of controlling a spectral output of the flashlets between about 650 nm and about 670 nm.

12. A method of stimulating and analyzing a fluorescence signal in a sample, the fluorescence signal being measured to analyze parameters of the sample, said method comprising the steps of:

(i) exciting the sample with a sequence of between 40–80 flashlets having a duration of about 0.5–1 $\mu$s each and time intervals ranging from about 0.5 $\mu$s to 2.0 $\mu$s, to saturate PSII reaction centers in the sample within about 40–80 $\mu$s;

(ii) exciting the sample a second time with between 40–80 flashlets having a duration of about 0.125–0.5 $\mu$s each and time intervals exponentially increased from about 50 $\mu$s to 20 ms; and (iii) repeating steps (i) and (ii) of exciting about 15–30 times with about 40–80 flashlets, wherein total time interval of each repeated step (ii) of exciting ranges between about 200 $\mu$s to 10 ms.

13. A method of stimulating a fluorescence signal in a sample, the fluorescence signal being measured to determine parameters of the sample, said method comprising the step of:

exciting the sample with about 2000–10000 flashlets; and individually controlling each flashlet length and each time interval between the flashlets so that energy output of each flashlet is maintained at a constant level.

14. A method of stimulating a fluorescence signal in a sample, the fluorescence signal being measured to determine parameters of the sample, said method comprising the step of:

exciting the sample with a sequence of N flashlets;

measuring the fluorescence signal of the excited sample; and continuously adjusting one of N, flashlet length and time intervals between flashlets to maintain the fluorescence signal at a predetermined level.

15. A fluorometer for stimulating and analyzing a fluorescence signal in a sample, comprising:

an excitation source for producing flashlets;

a flash control circuit for controlling number, length and time interval of the flashlets; and a fluorescence detector for measuring the fluorescent light generated by the sample in response to flashlets produced by the excitation source.

16. The fluorometer recited in claim 15, wherein excitation source is an LED flasher unit.

17. The fluorometer recited in claim 15, wherein the excitation source is a laser diode.

18. The fluorometer recited in claim 16, wherein the LED flasher unit comprises a series of LED banks each composed of LEDs with a different spectral output ranging from 440 to 540 nm.

19. The fluorometer recited in claim 16, wherein the LED flasher unit produces a continuous, background illumination in a blue-green spectral region (420 nm<$\lambda$<555 nm) simultaneously with the flashlets.

20. The fluorometer recited in claim 16, wherein the LED flasher unit produces a continuous, background illumination in a far red region ($\lambda$>700 nm) simultaneously with the flashlets.

21. The fluorometer recited in claim 15, wherein the flash control circuit controls the time interval between the flashlets to be between about 0.5 $\mu$s and 2.0 s.

22. The fluorometer recited in claim 15, further comprising a sample chamber for housing the sample, wherein the excitation source comprises a plurality of LED's configured cylindrically around the sample chamber.

23. The fluorometer recited in claim 15, further comprising a watertight housing surrounding the excitation source, flash control circuit, and the fluorescence detector.

24. The fluorometer recited as defined in claim 22, further comprising a brush for cleaning the sample chamber and a stepper motor controlling rotational and translational movements of the brush.

25. The fluorometer recited in claim 17, wherein the laser diode is operated with a bias current below a lasing threshold level to generate a continuous background irradiance.

26. The fluorometer recited in claim 25, wherein the laser diode is operated so that the background irradiance is proportional to the bias current.

27. The fluorometer recited in claim 15, further comprising:

a control and data processing unit that processes the fluorescence signal to calculate measures of photosynthetic parameters.

28. The fluorometer recited in claim 27 wherein the photosynthetic parameters include one of $F_0$ (minimal) and $F_m$ (maximal) components of PSII fluorescence, spectrally resolved functional ($\sigma_{PSII}$) and absorption ($a_{PSII}$) cross sections, energy transfer between PSII units, kinetics of electron transport between $Q_a$ and PQ pool and between PQ pool and PSI, PQ pool size, and photochemical and non-photochemical quenching.

29. A system for stimulating and analyzing a fluorescence signal in a sample comprising:

an excitation source that generates both a sequence of flashlets and a steady state background irradiance, wherein the protocol includes flashlets having a duration of about 0.125 $\mu$s–2.0s and time intervals between the flashlets ranging from about 0.5 $\mu$s–100 $\mu$s;

an excitation control circuit that controls both the sequence of flashlets and the steady state background irradiance;

an excitation/emission optical system that guides the flashlets to the sample and guides an emitted fluorescent light from the sample;

a fluorescence detector that detects the emitted fluorescent light and generates a fluorescence signal;

a data acquisition circuit that processes the fluorescence signal and generates a digitized fluorescence and reference signal; and a controller that processes the digitized fluorescence and reference signal to calculate photosynthetic parameters of the sample.

30. The system recited in claim 29, wherein the controller also determines a protocol that defines the sequence of flashlets.

31. The system recited in claim 29, wherein the photosynthetic parameters include at least one of $F_0$ (minimal) and $F_m$ (maximal) components of PSII fluorescence, spectrally resolved functional ($\sigma_{PSII}$) and absorption ($a_{PSII}$) cross sections, energy transfer between PSII units, kinetics of electron transport between $Q_a$ and PQ pool and between PQ pool and PSI, PQ pool size, and photochemical and non-photochemical quenching.

32. The system recited in claim 29 wherein the excitation source is an LED flasher unit.

33. The system recited in claim 32 wherein the LED flasher unit comprises a series of LED banks each composed of LEDs with a different spectral output ranging between about 440 to 540 nm.

34. The system recited in claim 29 wherein the excitation source is a laser diode.

* * * * *